(12) United States Patent
Galen et al.

(10) Patent No.: US 11,061,014 B2
(45) Date of Patent: Jul. 13, 2021

(54) MALARIA SPECIES DETECTION

(71) Applicant: HEMEX HEALTH, INC., Portland, OR (US)

(72) Inventors: Peter Galen, Portland, OR (US); James Daren Bledsoe, Portland, OR (US); D'Arbra Blankenship, Cleveland, OH (US); Robert J. Deissler, Cleveland, OH (US); Steven M. Goss, Salem, OR (US); Brian T. Grimberg, Shaker Heights, OH (US)

(73) Assignee: HEMEX HEALTH, INC., Portland, OR (US)

( * ) Notice: Subject to any disclaimer, the term of this patent is extended or adjusted under 35 U.S.C. 154(b) by 0 days.

(21) Appl. No.: 16/912,487

(22) Filed: Jun. 25, 2020

(65) Prior Publication Data

US 2020/0408735 A1 Dec. 31, 2020

Related U.S. Application Data

(60) Provisional application No. 62/866,534, filed on Jun. 25, 2019.

(51) Int. Cl.
*G01N 33/487* (2006.01)
*B01L 3/00* (2006.01)
(Continued)

(52) U.S. Cl.
CPC ...... *G01N 33/4875* (2013.01); *B01L 3/50273* (2013.01); *G01N 33/48792* (2013.01); *G01N 33/49* (2013.01); *G01N 35/00871* (2013.01); *B01L 2200/143* (2013.01); *B01L 2300/021* (2013.01); *B01L 2300/025* (2013.01); *B01L 2300/0672* (2013.01); *B01L 2300/087* (2013.01); *B01L 2300/0816* (2013.01); *G01N 2035/00881* (2013.01); *G01N 2035/00891* (2013.01); *G01N 2333/445* (2013.01)

(58) Field of Classification Search
None
See application file for complete search history.

(56) References Cited

U.S. PATENT DOCUMENTS 6,656,428 B1 * 12/2003 Clark ............... B01L 3/502
422/404
10,345,237 B1   7/2019 Cooper
(Continued)

FOREIGN PATENT DOCUMENTS

WO   2017083317 A1   5/2017

OTHER PUBLICATIONS

International Search Report and Written Opinion dated Oct. 1, 2020, International Application No. PCT/US20/39675, International Filing Date Jun. 25, 2020.

*Primary Examiner* — Matthew D Krcha
(74) *Attorney, Agent, or Firm* — Lane Powell PC

(57) ABSTRACT

A diagnostic system that includes a cartridge and a reader. The cartridge can contain a patient sample, such as a blood sample. The cartridge is inserted into the reader and the patient sample is analyzed. The sample can be processed for data collection and analysis to provide interpretative results indicative of a disorder, condition, disease or infection of the patient. For example, the data collection and analysis can determine one or more hemozoin characteristics.

25 Claims, 10 Drawing Sheets

(51) Int. Cl.
*G01N 33/49* (2006.01)
*G01N 35/00* (2006.01)

(56) References Cited

U.S. PATENT DOCUMENTS

| | | | |
|---|---|---|---|
| 2005/0009057 A1* | 1/2005 | Dutta | G01N 33/56905 |
| | | | 435/6.15 |
| 2007/0078354 A1 | 4/2007 | Holland | |
| 2007/0292941 A1* | 12/2007 | Handique | B01L 3/50273 |
| | | | 435/288.7 |
| 2009/0318784 A1* | 12/2009 | Newman | A61B 5/0095 |
| | | | 600/309 |
| 2010/0255601 A1* | 10/2010 | Beaudet | G01N 21/6452 |
| | | | 436/172 |
| 2011/0196239 A1 | 8/2011 | Behrend et al. | |
| 2012/0156933 A1* | 6/2012 | Kreger | A61B 5/0245 |
| | | | 439/625 |
| 2014/0315238 A1 | 10/2014 | Farrell et al. | |
| 2017/0113221 A1 | 4/2017 | Hoffman et al. | |
| 2017/0120240 A1* | 5/2017 | Delamarche | B01L 3/50273 |
| 2018/0064384 A1 | 3/2018 | Galen et al. | |
| 2018/0067101 A1* | 3/2018 | Galen | G01N 33/49 |

* cited by examiner

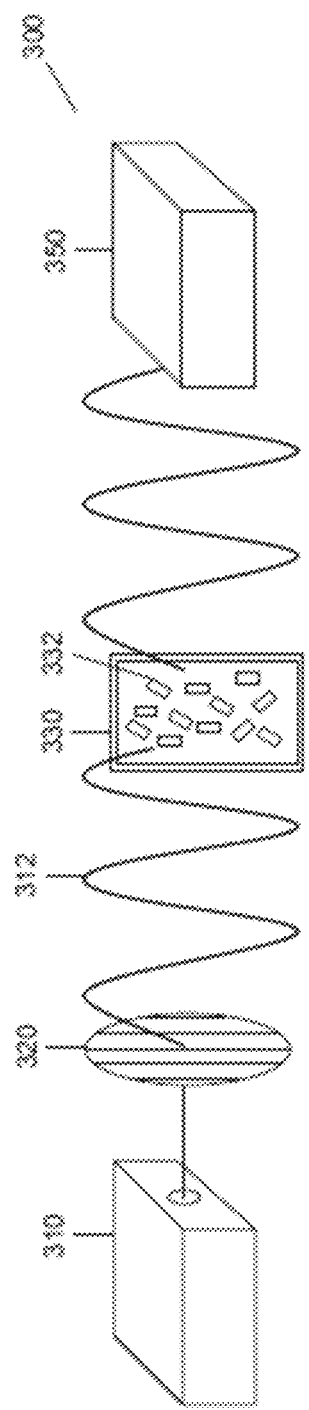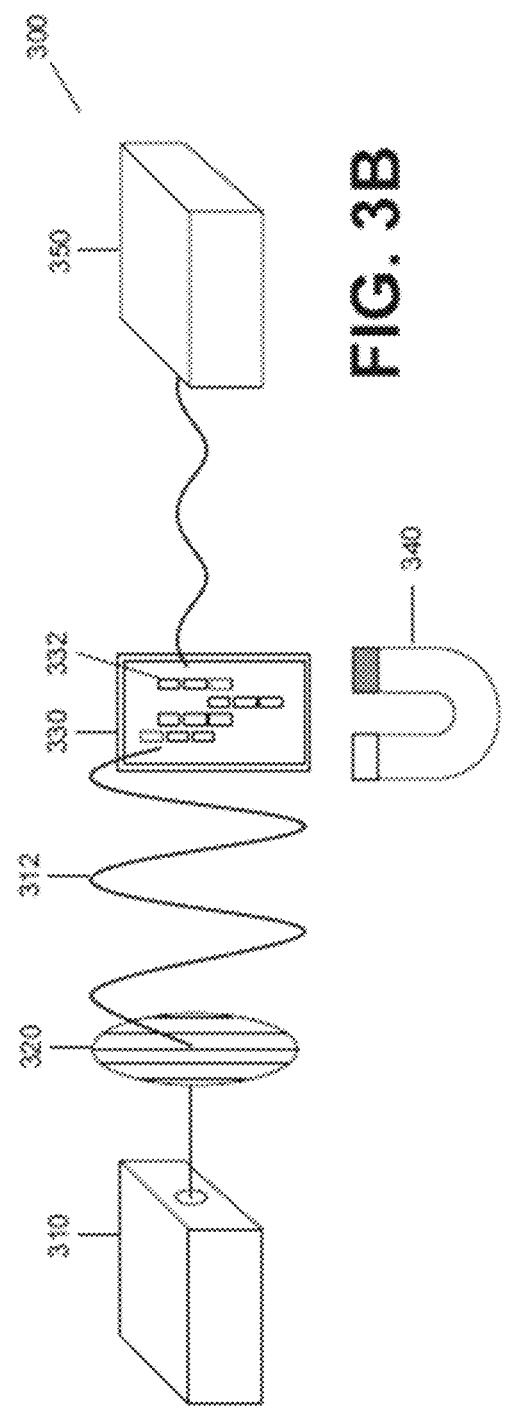

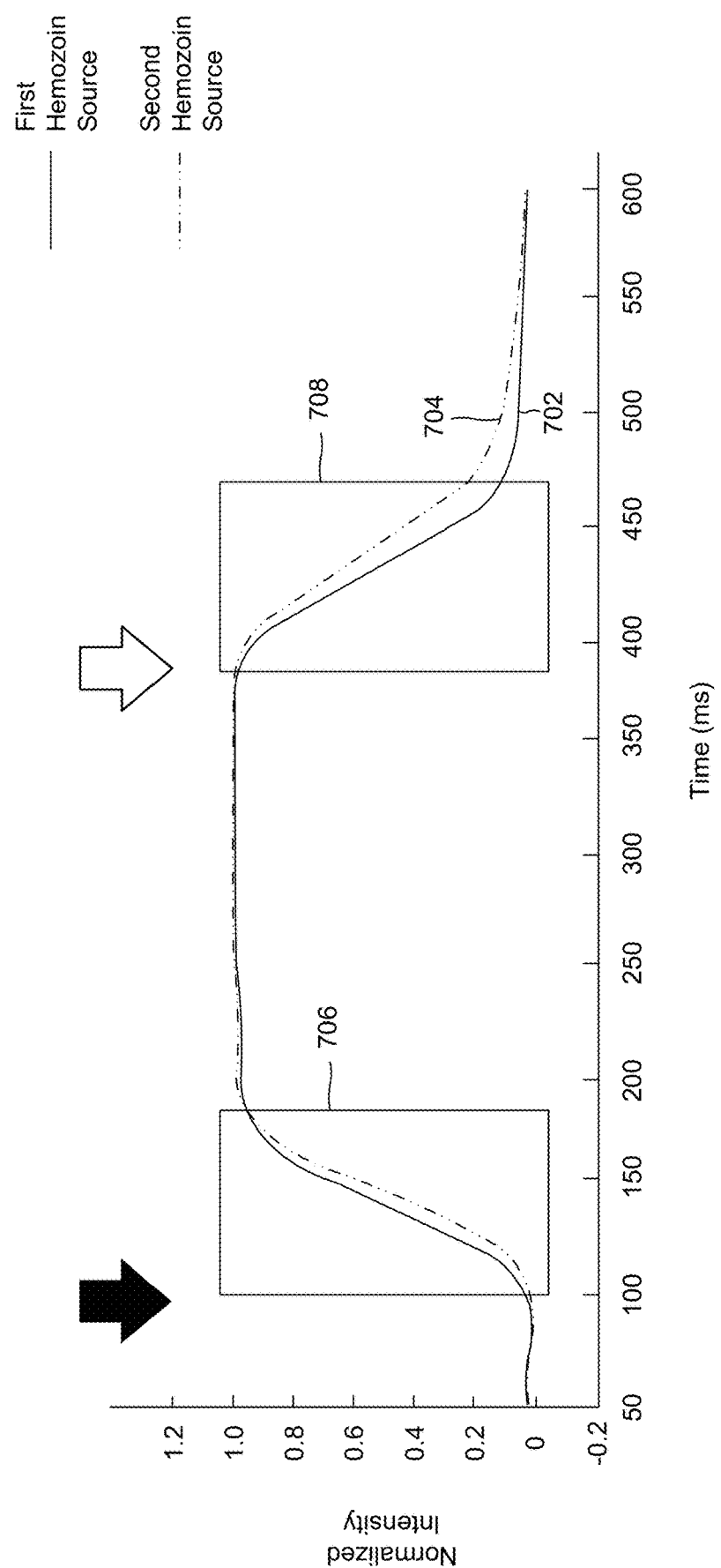

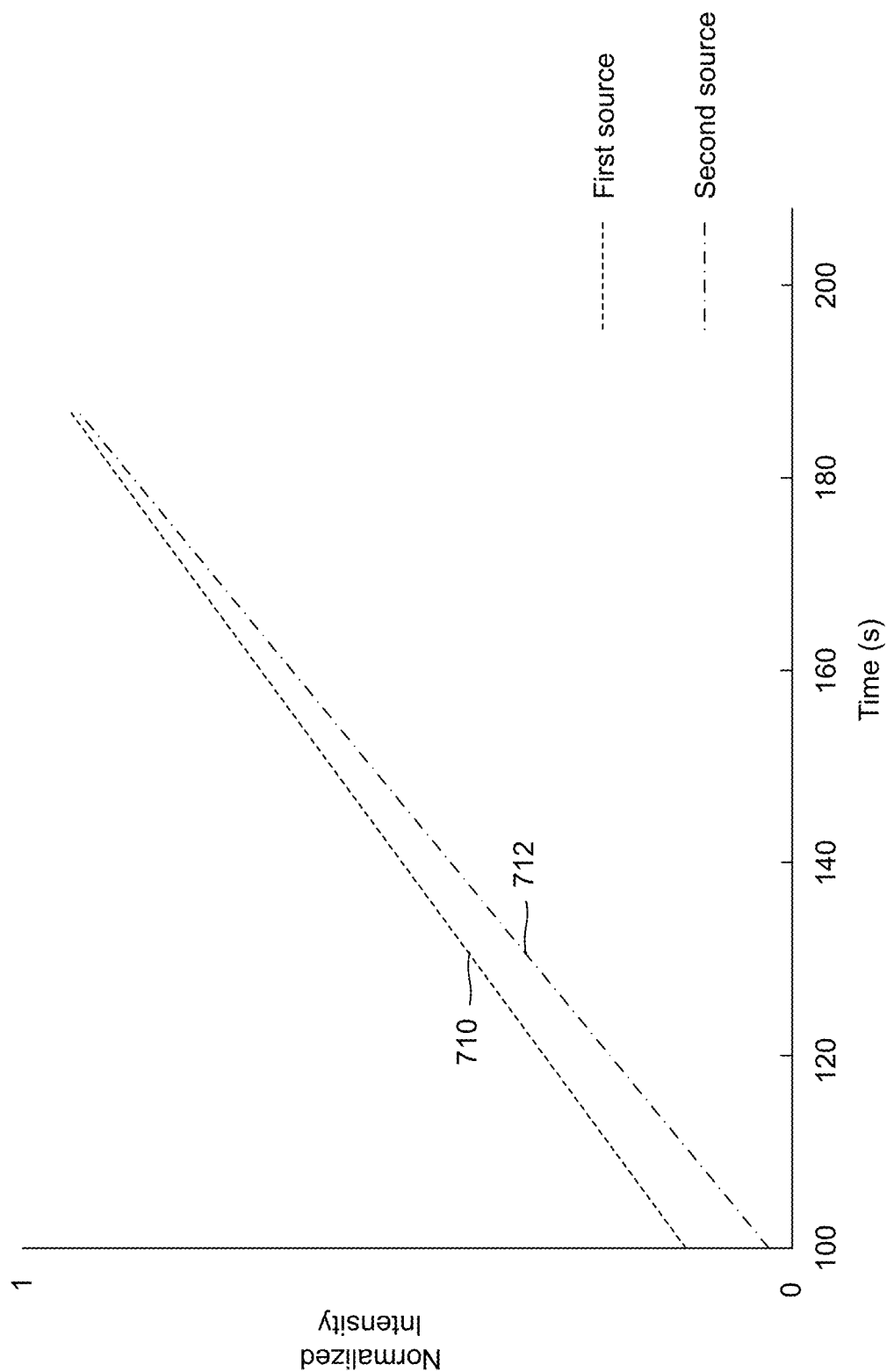

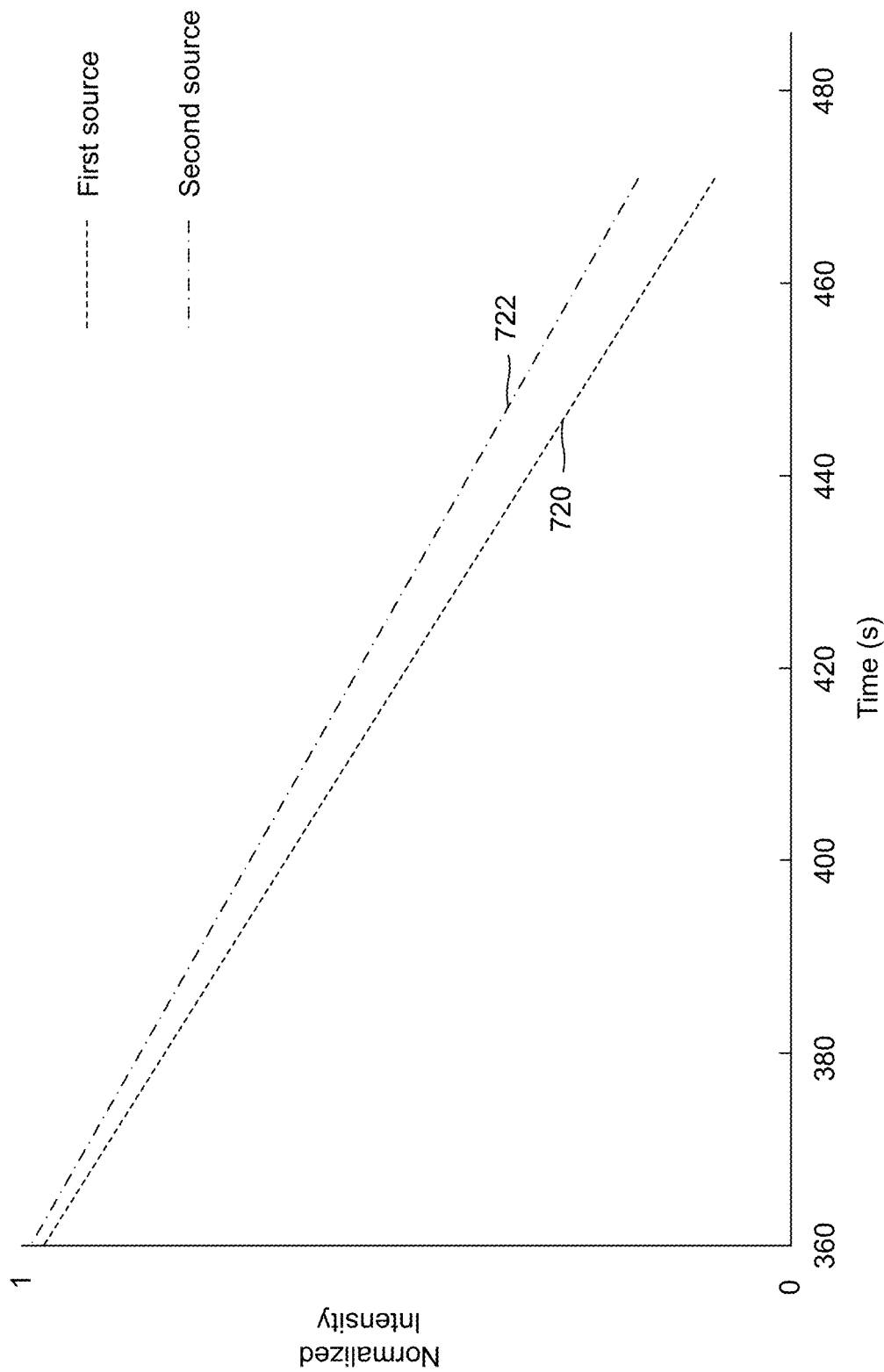

MALARIA SPECIES DETECTION

CROSS-REFERENCE TO RELATED APPLICATIONS

This application claims the benefit of U.S. Provisional Patent Application Ser. No. 62/866,534, filed Jun. 25, 2019, the contents of which are herein incorporated by reference in their entirety.

BACKGROUND

Patient diagnostics save lives, reduce the time to treatment for the patient and provide valuable insight for targeted treatment. In many developed countries, modern medical facilities can provide patients with the most advanced diagnostic services allowing patients to be efficiently and effectively treated. In less developed countries or regions, high quality medical facilities and diagnostic services can be lacking, often due to economic and infrastructure considerations. In many less developed countries, the economy cannot afford the latest in medical technology and infrastructure, such as a robust power grid or highly trained clinicians, required to support the high demands of modern medical technology. Sadly, a large portion of the world's population resides in underserved or underdeveloped areas where the lack of efficient and effective diagnostic services critically impacts the population morbidity, mortality and overall health. This lack of medical care can lead or contribute to knock-on effects, such as low economic and educational development.

Often, many less developed countries and areas also lack sufficient trained users that are typically required to perform the necessary diagnostic services. This can lead to inconclusive or erroneous results from diagnostic services or to significant delays in diagnosis as the diagnostic services are required to be performed in another location that has the requisite infrastructure and knowledge to perform the diagnostic service. For patients, this can mean further delays in treatment, which can decrease their chances of survival, increase the spread of the disease, or lead to increased debilitation caused by the disease or condition.

Where large laboratories may be prohibitively expensive and difficult to staff, point-of-care diagnostic devices may provide an effective solution. Such a solution could provide timely, accurate, and cost-effective health care.

One of the treatable common ailments disproportionately affecting less developed countries are hemoglobin disorders, such as sickle cell disease (SCD), thalassemia and other hemoglobinopathies. These are genetic disorders that are believed to have evolved in response to malaria. With population migration, these conditions have spread to the global population and affect the livelihood and health of a large number of people. With early detection or diagnosis, these conditions can be treated and managed before they have significant adverse impact on the stricken individual. As with malaria, these disorders affect the populations of less developed countries and areas, which have limited to no access to the diagnostic services to rapidly, effectively and efficiently diagnose the conditions.

What is needed is a point-of-care device or system to effectively and efficiently diagnose a disease, condition, or ailment.

BRIEF DESCRIPTION OF THE DRAWINGS

FIGS. 3A-3B illustrate an example magneto-optical detection (MOD) system.
FIGS. 7A-7C illustrate testing results.

DETAILED DESCRIPTION

Figure 1A:
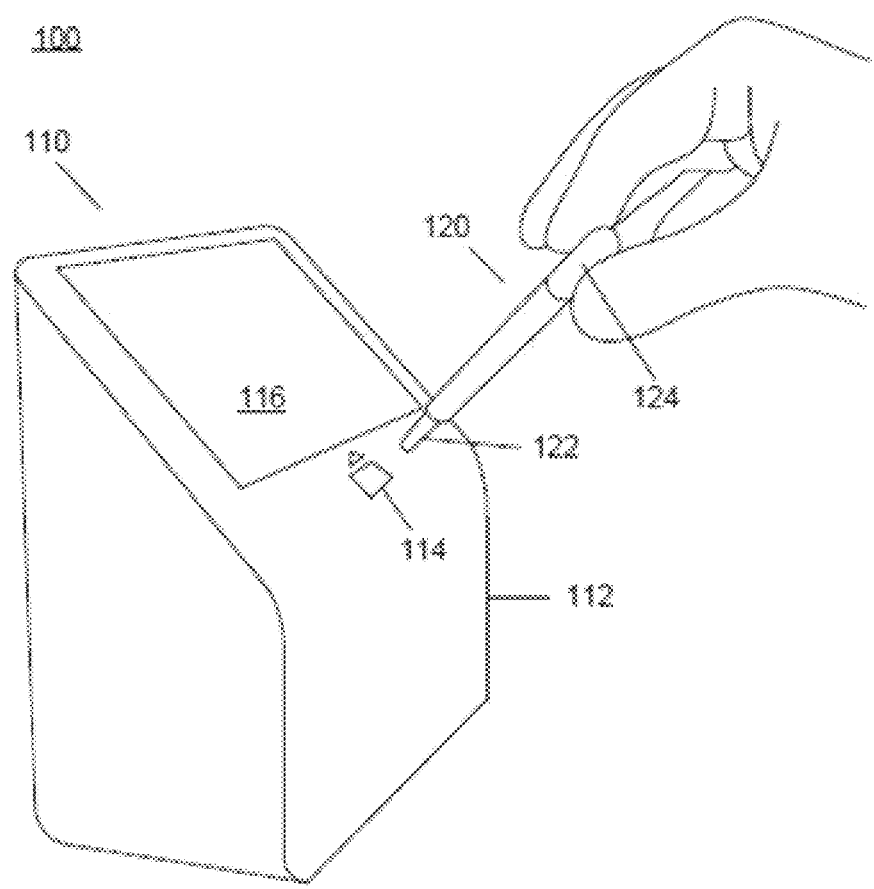
FIG. 1A illustrates an example diagnostics system.

Various example point-of-care, in vitro diagnostic devices and methods for detecting and helping to diagnose blood disorders, and specifically inherited blood disorders, infections, or other conditions or diseases are described herein. Controlling, optimizing, or controlling and optimizing parameters of a test, parameters of a system, or both can enhance or increase detection of an analyte or component of a sample.

For example, a system for detecting hemozoin can include a reader and a control module. The reader is a device for testing a sample. The control module can control, optimize, or control and optimize one or more parameters of a test, the reader, or both. The control module controls, among other things, magnet motion, speed, number of cycles, data acquisition rates, light source brightness, and then advanced signal processing techniques such as baseline wander removal, signal noise reduction techniques and other techniques to make at the first point at which an analyte, such as hemozoin, is detected or determined to be absent.

The control module can also indicate a retest is required based on an undesired fluctuation or shape in the data signal. The undesired data fluctuation can be due to voltage saturation (i.e., voltage applied to the patient sample exceeds a threshold), voltage drift (i.e., change in voltage over time that exceeds a threshold change), a bad cartridge, indicate when a new sample is required, the like, or combinations or multiples thereof.

The system can also include a sonication module that controls sonication, detects the effectiveness of sonication, retriggers additional sonication cycles before a test starts, the like, or combinations or multiples thereof.

In the following description, the term "sample" is used to describe at least one material to undergo testing, processing, combinations thereof, or the like. The sample can be plant-based, organism-based, inorganic or animal-based. For example, the sample can be derived or obtained from a plant, algae, mineral, or the like. As another example, the sample, such as one derived or obtained from an organism, an animal, or a human, can be a biological fluid, a biological semi-solid, a biological solid which can be liquefied in any appropriate manner, a suspension, a portion of the suspension, a component of the suspension, or the like. For the sake of convenience, the sample referenced is whole blood, though it should be understood that the method and system described and discussed herein is used with any appropriate sample, such as urine, blood, bone marrow, buffy coat, cystic fluid, ascites fluid, stool, semen, cerebrospinal fluid, nipple aspirate fluid, saliva, amniotic fluid, mucus membrane secretions, aqueous humor, vitreous humor, vomit, vaginal fluid, and any other physiological fluid or semi-solid. For example, the sample is a tissue sample or a material from adipose tissue, an adrenal gland, bone marrow, a breast, a caudate, a cerebellum, a cerebral cortex, a cervix, a uterus, a colon, an endometrium, an esophagus, a fallopian tube, a heart muscle, a hippocampus, a hypothalamus, a kidney, a liver, a lung, a lymph node, an ovary, a pancreas, a pituitary gland, a prostate, a salivary gland, a skeletal muscle, skin, a small intestine, a large intestine, a spleen, a stomach, a testicle, a thyroid gland, or a bladder.

In the following descriptions, the terms "analyte" or "target material" are used to describe a biological material of interest. It should also be understood that the analyte can be a fraction of a sample, a cell, such as ova, fetal material, an immune cell, a mesenchymal cell, a stem cell, a vesicle, such as an exosome, a liposome, a protein, a nucleic acid, a biological molecule, a naturally occurring or artificially prepared microscopic unit having an enclosed membrane, parasites (e.g. spirochetes; malaria-inducing agents), microorganisms, viruses, a component of a cell or parasite, or inflammatory cells.

Cartridge and MOD System

FIG. 1A illustrates an example reader 110 and cartridge 120 of a point-of-care blood diagnostic system 100. A point-of-care blood diagnostic system includes devices that can be physically located at the site at which patients are tested, though they can be used in a laboratory setting also, and sometimes treated to provide quick results and highly effective treatment. Point-of-care devices can provide information and help in diagnosing patient disorders or infections while the patient is present with potentially immediate referral and treatment. Unlike gold standard laboratory-based blood testing for disorders or infections, the disclosed point-of-care devices enable diagnosis close to the patient while maintaining high sensitivity and accuracy, which aids efficient and effective early treatment of the disorder or infection.

The reader 110 includes a housing 112, a cartridge receptacle 114 and a display 116. The cartridge 120, which contains the patient sample and, optionally diluents, stains (e.g., fluorescent, chromogenic, or the like), reagents (e.g., to increase or decrease viscosity) or materials, is inserted into the cartridge receptacle 114 of the reader 110 to transfer the patient sample, treated or untreated, into the reader 110 to perform a diagnostic test or analysis. The cartridge 120 more generally is placed in proximity to the reader in such a manner that the reader can interact with one or more elements of the cartridge to perform analysis of the patient sample. The cartridge 120 can include a pipette-like end 122 and a bulb 124 for siphoning a patient sample into the cartridge 120 in preparation for the diagnostic test. Alternatively, the cartridge 120 can include a capillary tube by which the patient sample can be obtained for analysis or testing. In a further embodiment, collection of the patient blood sample can be performed using blotting paper that is included in the cartridge 120 to collect a blood spot that can be analyzed by the point-of-care blood diagnostic system 100.

The housing 112 of the reader 110 can be constructed of materials such as plastic or metal and is preferably sealed with a smooth surface, which allows the reader 110 to be easily cleaned or disinfected and resist external water and or dust. Further, the housing 112 is sufficiently strong to allow the safe transport and use of the reader 110 without substantial damage to the reader 110 and the diagnostic systems within. Additionally, the housing 112 can have properties that shield or minimize the exposure of the interior of the reader 110 to temperature or humidity variations or light intrusion. The robustness of the reader 110 allows it to be used in a variety of locations and environments without adversely affecting the results of the diagnostic system.

The housing 112 of the reader 110 can also include vibration isolation to minimize vibration of the reader 110 during the measurement process to assist with preventing analysis error of the patient sample. Vibration isolation can include suspending or isolating the components and systems of the reader 110 within the housing 112 or containing the components and systems within an internal housing that is suspended or isolated from the external housing 112. Alternative vibration isolation can include anti-vibration feet or mounts on which the reader 110 can sit on a surface. Additional vibration isolation can include placing the reader 110 on a cushioned or anti-vibration mat to reduce or limit the vibration and disturbance of the reader 110 by its external environment.

The cartridge receptacle 114 can be conformably shaped to receive the cartridge 120. The cartridge 120 can be received partially or completely into the cartridge receptacle 114 or the reader 110. Alternatively, the cartridge 120 can be otherwise connected, such as by an external receptacle or conduit, to the reader 110 to transfer the patient sample, or portion thereof, into the reader 110. Such an external receptacle or conduit can be electrically coupled to the electronics housed in the reader 110 by a wireless or hard-wire connection of any suitable configuration.

Figure 1B:
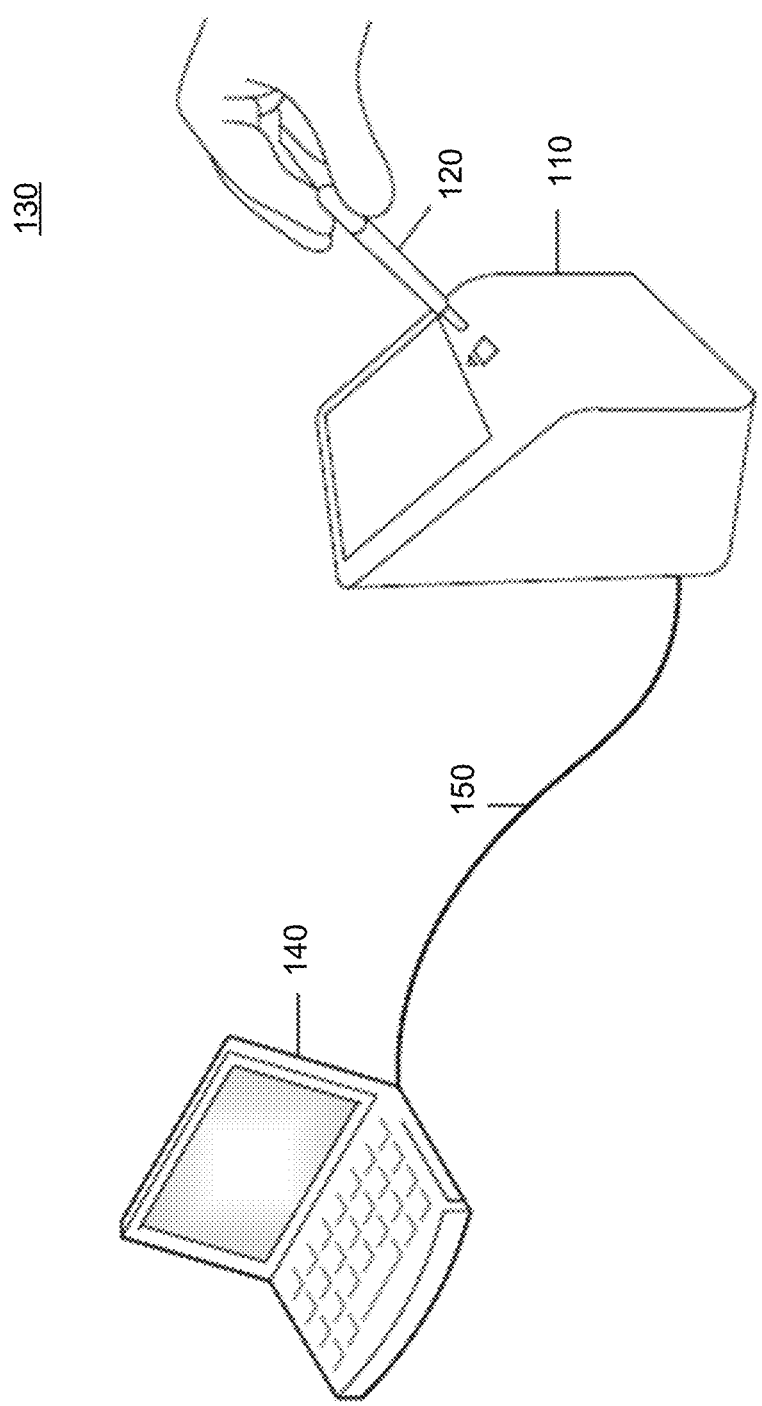
FIG. 1B illustrates an example diagnostics system.

FIG. 1B illustrates an example diagnostic system 130 that includes the cartridge 120 and the reader 110, such as described herein, the reader 110 connected 150 to an external device 140, such as a computing device, including a laptop, phone, tablet, a server, remote computer, or other external device. The connection 150 between the reader 110 and the external device 140 can be a physical connection, such as a universal serial bus (USB) connector or can be a wireless connection, such as an IR, Bluetooth® or WiFi electrical coupling, or a combination thereof. The connection 150 allows communication between the reader 110 and the external device 140. In an example, the reader 110 can perform analysis of a patient sample contained within the cartridge 120, data from the various analysis systems or elements of the reader 110 can be transmitted through the connection 150 to the external device 140 for processing. The external device 140 can then display or transmit the processed results, or portion thereof, to a user or can optionally transmit the processed results back to the reader 110 for display or transmission of the analysis results, or a portion thereof, to the user. In a further example, the reader 110 and external device 140 can both process all or a portion of the patient sample analysis data. The external device 140 can also control one or more aspects of the reader 110, such as the analysis able to be performed by the reader 110, authorized users of the reader 110 or other aspects of the reader 110 and its performance. Additionally, the external device 140 can be in the proximity of the reader 110, such as nearby, or can be remote from the reader 110, such as in another room or in another location including in another country. The external device 140 can communicate with or be connected to multiple readers and or other external systems, such as remote servers or databases.

The reader 110 can be a part of a network. The network can include wired and/or wireless connections. One or more servers can be incorporated into the network to store or process data and information. Processing can be done remotely. The network can include a plurality of readers, a plurality of servers, a plurality of displays, and the like.

Figure 2A:
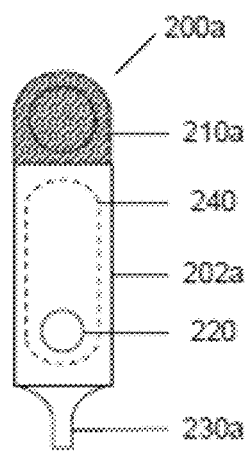
FIGS. 2A-2B illustrate example cartridges.
Figure 2B:
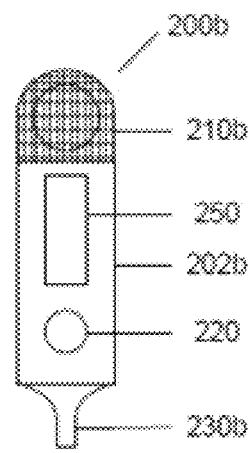

FIGS. 2A-2B illustrate example cartridges 200a and 200b. Each of the example cartridges 200a, 200b includes a housing 202a, 202b, an upper portion 210a, 210b and a lower portion 230a, 230b. The cartridges 200a, 200b can include a sample chamber, such as 240 of FIG. 2A, which is internal to the cartridge 200a, 200b and can store a patient sample within the cartridge 200a, 200b, such as a blood sample. The cartridges 200a, 200b transport or store a patient sample for analysis, or reading, by a reader. Further, the cartridges 200a, 200b can interface with the reader to assist with or facilitate the reading or analysis of the patient sample stored within the cartridge 200a, 200b. That is, the cartridge 200a, 200b can include features, such as an optical window 220 and an electrophoresis element 250 of cartridge 200b of FIG. 2B to assist with the analysis of the patient sample within the cartridge 200a, 200b. The cartridge 200a, 200b can also transfer all or a portion of the patient sample to the reader for analysis of the patient sample. The patient sample, or portion thereof, from the cartridge 200a, 200b can be transferred to a blood sample chamber of the reader or to another location of the reader, or external from the reader, for analysis of the patient blood sample.

The cartridges 200a, 200b can be condition, disease or ailment specific or multiple condition, disease or ailment specific. The cartridges 200a, 200b can include various internal or external features that customize a particular cartridge for the analysis of a specific, singular or multiple, condition, disease or ailment. The cartridge can include the patient sample size volume of the cartridge, various diluents, stains (e.g., fluorescent, chromogenic, or the like) or reagents (e.g., to increase or decrease viscosity) in the cartridge, the interface of the cartridge with the reader and other design or construction specification of the cartridge in relation to one or more particular conditions, diseases or ailments.

The housing 202a, 202b of the cartridge 200a, 200b can include structural, material or geometric features that assist or facilitate the analysis and acquisition of the patient sample. Such features can include internal chambers, such as the sample chamber 240 of FIG. 2A, to store the patient sample or other fluids or compounds, that are sized to ensure adequate sample size for the analysis of the collected patient blood sample, interfaces that interact with, engage, or facilitate the systems of the reader during analysis of the patient sample. Other features can include environmental controls that maintain the collected patient sample in a suitable condition for analysis, and other features or considerations. For example, an internal chamber of the reader could manually or automatically interface with the inserted cartridge via a port to cause diluents, stains (e.g., fluorescent, chromogenic, or the like), reagents (e.g., to increase or decrease viscosity), or other chemical treatments to mix with the patient sample in the cartridge. Such a port would be a passage, like a tube, that connects the sample chamber of the cartridge with the port so fluids can be added to the cartridge. The addition of such external fluids can be triggered automatically or manually when a user actuates a switch or other actuator, which the user may do in response to a user prompt to do so. The cartridge housing 202a, 202b can be formed of a suitable material such as a plastic, composite or metal to create a robust, disposable cartridge 200a, 200b. Additionally, the housing 202a, 202b material can be selected for the ability to be sterilized, such as sterilizing the cartridge 200a, 200b prior to use, for reuse or for killing pathogens prior to disposal.

Environmental considerations can also be used in the determination of a suitable material(s) for the cartridge housing 202a, 202b. Such environmental considerations can include the biodegradability of the housing material, the recyclability of the housing material, the incineration by-products of the housing material and other environmental considerations. These environmental considerations can reduce the environmental impact of the disposal, recycling or reuse of the cartridges 200a, 200b after use.

The housing 202a, 202b of the cartridge 200a, 200b can include a patient identification marker or an area to apply or mark patient identification onto the cartridge 200a, 200b. This marker could be in machine readable or human readable form or both. The patient identification allows the correlation of the analysis of the collected patient sample with a particular patient. Additionally, the reader can detect the patient identification marker to correlate the analysis with a patient, including automatically appending the analysis results to a patient's medical records. In an example embodiment, the patient identification can be obfuscated to remove patient personal information, such as a name, from the cartridge 200a, 200b, instead the patient can be assigned a random number, or sequence of characters, that is correlated to the particular patient in the reader, a computer or other system. The marker can also contain information on what test(s) to run and what to do with any results collected.

Patient diagnostic and demographic information can also be used for analysis to determine trends or emergence of conditions, disorders, diseases or ailments. This analysis can be used to prevent or minimize the spread of the condition or disorder or targeted diagnosis or treatment of the condition or disorder. For various conditions once properly diagnosed, such as a sickle cell and other hemoglobin conditions, geographical correlation of the prevalence of the condition can be used to perform measures to mitigate and minimize the effects of the condition on the target population.

The upper portion 210a, 210b of the cartridge 200a, 200b can include identification marker(s), such as a color, pattern, name, or other distinguishing features. The identification marker can be used to indicate the use of the cartridge 200a, 200b for the analysis of a specific condition(s), disease(s), or ailment(s). This can provide a clear, visual indication to a user that the cartridge 200a, 200b is to be used with specific analysis or analyses.

Additionally, the upper portion 210a, 210b can be a portion of a sample collection element, such as a suction bulb, actuation element, or capillary tube to assist or facilitate the collection of the patient sample into the cartridge 200a, 200b. As a suction bulb, the upper portion can be formed of a resilient or flexible material capable of deforming in volume to assist in the uptake of a patient sample within the cartridge 200a, 200b. As an actuation element, the application of pressure or other input by a user, other or device to the upper portion 210a, 210b of the cartridge 200a, 200b can actuate the passive or active acquisition of a patient sample into the cartridge 200a, 200b in preparation for analysis, such as extending or retracting a needle or capillary tube. A capillary tube or plane is one means of passively collecting the sample with no user or machine pressure required.

Further, the upper portion 210a, 210b can contain a diluent, marker, reagent or other fluid or substance that is stored internally in a chamber and that can be released into or mixed with the patient sample within the cartridge 200a, 200b. Application of pressure to the upper portion 210a, 210b of the cartridge 200a, 200b can introduce the contained substance or fluid into the patient sample within the cartridge 200a, 200b which mixes the patient sample with the contained substance(s) or fluid(s). Example diluent ratios can include from 1:0.5 to 1:100. The contained substance or fluid can assist with the analysis of the patient sample, preparation of the patient sample for analysis, preservation of the sample for analysis or other desirable or necessary patient sample modification for efficient and effective analysis of the patient sample.

Additionally, the upper portion 210a, 210b of the cartridge 200a, 200b can be contoured or shaped to provide a comfortable, ergonomic, or easy grip for a user to handle the cartridge 200a, 200b during insertion or extraction into/from the reader or diagnostic device. Alternatively, the surface texture of the upper portion 210a, 210b can be such that it improves the ability of a user to grip the cartridge 200a, 200b.

The optical window 220 can be included on the cartridge 200a, 200b, which allows light to pass into or through a portion of the cartridge 200a, 200b such as a sample chamber containing the patient sample, such as 240 of FIG. 2A. The ability to pass light into or through the sample volume within the cartridge 200a, 200b can be a necessary step during analysis of the patient sample within the cartridge 200a, 200b. The optical window 220 can be a material or construction that necessarily or desirably alters light entering the optical window 220 as a part of the analysis of the patient sample within, such as collimating, filtering, or polarizing the light that passes through the optical window 220. Alternatively, the optical window 220 can be transparent or translucent, or can be an opening within the housing 202a, 202b of the cartridge 200a, 200b. The cartridge 200a, 200b can include a reflector opposite the optical window 220, 220b that reflects the incoming light back through the optical window 220a, 220b or through another optical window, or can include a further optical window opposite the light entry window to allow light to pass through the cartridge 200a, 200b.

An electrophoresis element, such as 250 of cartridge 200b of FIG. 2B, can assist with performing an electrophoresis analysis of a patient sample within the cartridge 250. The electrophoresis element 250 can include electrodes to establish an electrical gradient across the element to perform the electrophoresis analysis. A cover can be included to protect the electrophoresis element, while still allowing the results to be viewed either through the cover or by removal of the cover. The cover can be optically transparent to allow optical viewing of the results or the electrophoresis process being performed. Light can be reflected off of or transmitted through the electrophoresis element 250 to assist with viewing the results displayed thereon. The cartridge 200b can include one or more structural features to facilitate the transmission of light through the electrophoresis element 250.

The lower portion 230a, 230b can house or be a portion of the sample collection system. In the examples shown in FIGS. 2A and 2B, the lower portion 230a, 230b can include a channel or tube through which the patient sample can be transferred into the interior of the cartridge 200a, 200b. The lower portion 230a, 230b can also house a portion of the sample collection system, such as an extendable needle like a lancet or a capillary tube through which the patient sample can be transferred to the interior of the cartridge 200a, 200b.

The lower portion 230a, 230b can also include elements or systems to assist with the analyzing or storage of the patient sample. This can include an interface or mechanism to release at least a portion of the patient sample from within the cartridge 200a, 200b into the reader or a barrier or seal that restrains or preserves the patient sample within the cartridge 200a, 200b.

The lower portion 230a, 230b can further include an indicator that is visible once the cartridge 200a, 200b has been previously used. This can prevent cross-contamination of patient specimens, prevent the reuse of a single-use cartridge 200a, 200b, or both which could alter or otherwise compromise the results of the patient sample analysis. The indication can be structural in nature, with an alteration, such as a removal or break in a portion of the cartridge 200a, 200b housing 202a, 202b of the lower portion 230a, 230b that is a visible once the cartridge 200a, 200b has been used or has acquired a patient sample. Additionally, the lower portion 230a, 230b can deform after acquisition of a patient sample within the cartridge 200a, 200b, which prevents further collection of a patient sample(s) using the cartridge 200a, 200b. The indication could be electrical.

FIGS. 3A-3B illustrate an example magneto-optical detection (MOD) system 300. The MOD system 300 includes a light source 310 that emits light 312, a polarizer 320, a patient sample 330, a magnet 340 and a photodetector 350. The MOD system 300 can also include a lens between the light source 310 and the polarizer 320. In one example, the light source 310 can produce multiple lights of different wavelengths. The light source 310 can include multiple LEDs, for example, each emitting a different wavelength. Or, the light source 310 can emit multiple wavelengths and one or more filters can be employed to permit passage of one or more spectra. In another example, the MOD system 300 can include a plurality of light sources 310, which each light source 310 emitting a different spectrum of light.

Some diseases and conditions result in the release of or changes in a magnetic, or paramagnetic, component of a patient's sample. An example patient sample can include blood which includes hemozoin that contains iron—a magnetic compound, the amount or concentration of which can be used to determine the presence or intensity of a condition or disease, such as malaria. The transmission of light 312 through a patient sample 330 in a varying magnetic field can be used to detect the presence of and determine, absolute or relative, concentrations of magnetic and non-magnetic components within the patient sample 330.

FIG. 3A illustrates the transmission of light 312, from the light source 310, through the patient sample 330 in a magnetic field in a first state, such as a low strength magnetic field. In this example, a magnetic component 332 of the patient sample 330 is randomly arranged allowing for a measurable transmittance of light 312 through the patient sample 330. The transmitted light 312 is received by the photodetector 350 and characterized, such as by properties including frequency, intensity, distribution, wavelength or other light properties or characteristics. This first light value is a base value that can be used to measure the relative change in at least a property or characteristic of the light transmitted through the patient sample 330 with an alternate, varying or changeable magnetic field applied.

FIG. 3B illustrates the transmission of light 312, from the same light source 310, through the patient sample 330 in the presence of an applied magnetic field in a second state, such as a higher strength magnetic field (for example, the "ON" or "HIGH" state can be 0.5 Tesla) than the first state (for example, the first state can be 0.01 Tesla). The strength of the magnetic field applied to the patient sample 330 can be increased from the first state to the higher strength second state by altering the proximity of a magnet(s) 340. The application of a higher strength magnetic field causes the ordered alignment or arrangement of the magnetic, or paramagnetic, components 332 of the patient sample 330. This ordering or alignment effects the transmission of light 312 through the patient sample 330, which is a second value that can be detected by the photodetector 350. An effect can include the reduction or increase of light 312 transmitted through the patient sample 330. The comparison or measurement of the first light value in a magnetic field in a first, lower, state, and the second light value in a magnetic field in a second, higher, state, can be used to determine one or more hemozoin characteristics (e.g., amount of hemozoin, size of hemozoin, source of hemozoin, or the like) or the presence of a disease or condition or the intensity of the disease or condition, such as the level of infection.

An example disease detectable by the MOD system 300 can include malaria. Malaria can be caused by a variety of different *plasmodium* parasites which infect the hemoglobin containing red blood cells of a host. The *plasmodium* replicate within the red blood cells, eventually destroying the red blood cells. The *plasmodium* parasite(s) release hemozoin as a byproduct after having ingested an infected patient's healthy hemoglobin. Hemozoin in a patient's blood is a biomarker of malaria. Hemozoin is a paramagnetic compound and is thus sensitive to magnetic fields. Hemozoin within a patient sample can be detected by a MOD system due to a differential light transmission characteristic (s) in different magnetic fields. The differential light transmission characteristic can be indicative of several infection characteristics, such as the presence of the parasite, the parasite infection levels, hemozoin characteristic (e.g., amount of hemozoin, size of hemozoin, source of hemozoin, or the like), and other infection characteristics. In other words, the size of hemozoin can be determined based on the differential light transmission characteristics, such as those determined by the alignment and randomization of the hemozoin due to the application and removal of the magnet. Different sized hemozoin crystals affects the differential light transmission characteristics. The differential light transmission characteristics can include change in light transmission, though need not be an absolute value of change in light transmission. In one example, the differential light transmission characteristics, including one or more thresholds, can be affected by hemozoin size, such as with equal or substantially equal concentrations (i.e., less light signal change).

A MOD system, such as the example of FIGS. 3A-3B, can be integrated into a reader, such as the example shown in FIGS. 1A-1B, or can be external to a reader. In the example in which the MOD system is external to a reader, the MOD system requires the ability to pass light through the patient sample, within a cartridge or reader, and detect properties or characteristics of the light transmitted through the patient sample in a varying or changeable magnetic field. Alternatively, the MOD system and components can be split between the reader and external to the reader, with a portion of the MOD system and components located internal to the reader and another portion of the MOD system and components located external to the reader.

Additionally, an example MOD system can include only the optical component. Light from a light source is transmitted through a patient sample and the transmitted light is received by a light detector that can determine and measure features, properties, or characteristics of the transmitted light or can transmit information from which the features, properties, or characteristics of the transmitted light can be determined or measured. In this example, the magnetic component of the MOD system is either absent from the system or is not used during analysis of a patient sample. Instead, the patient sample can be analyzed based on the light transmission differential or characteristics of the transmitted light.

Figure 4:
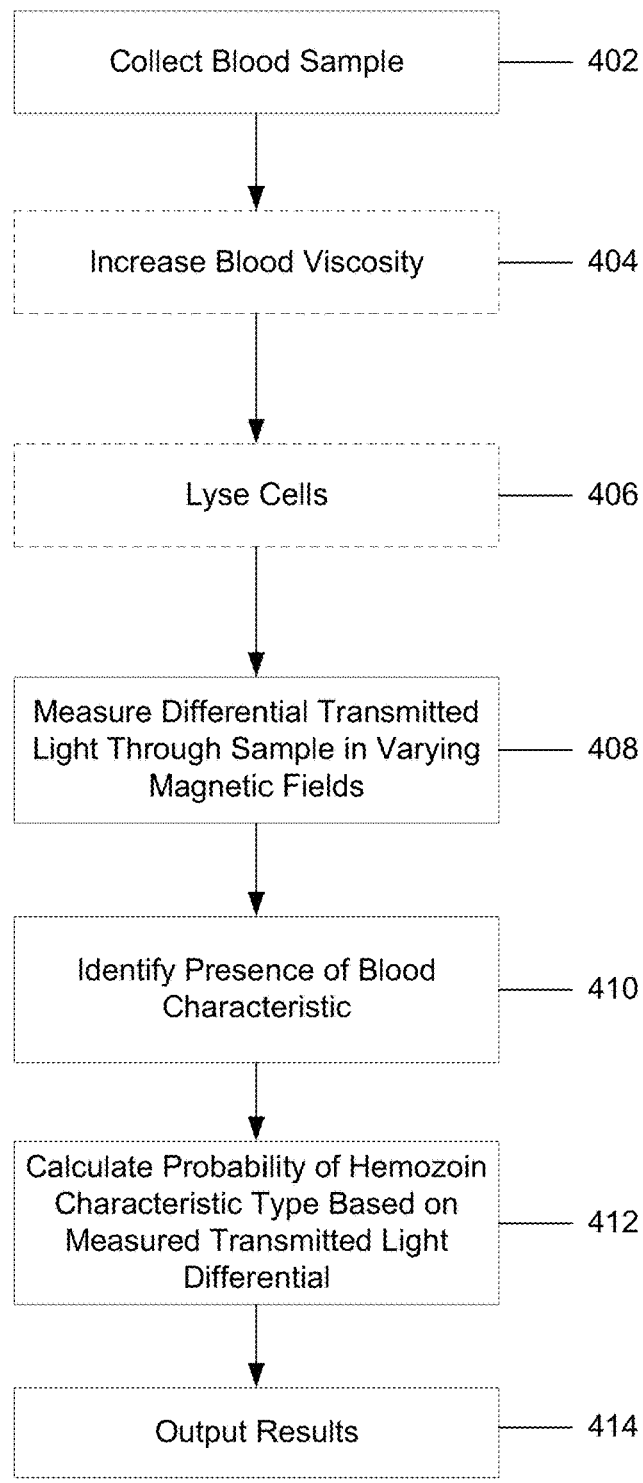
FIG. 4 illustrates an example analysis method using the example MOD system of FIGS. 3A-3B.

FIG. 4 is an example analysis method 400 using a MOD system, such as the one shown in FIGS. 3A-3B. The analysis of a patient sample, which is patient blood in this example, is performed to determine a blood characteristic, which can include the presence of a disease or condition, quantification of a disease or condition, likelihood of the presence of a disease or condition, a characteristic that can be indicative of a disease or condition, a quantification of a characteristic that can be indicative of a disease or condition, or other blood characteristic that can be effected by the presence of a disease or condition of the patient. The example method of FIG. 4 is performed using a reader and cartridge system, such as the example shown in FIGS. 1A-1B, and the MOD system is included within the reader which can include additional systems or elements to analyze, quantify, identify or otherwise determine characteristics of a patient sample that can be indicative of the presence of a disease or condition of the patient.

An initial step 402 of the method 400 can include the collection of a patient sample for analysis, in this example, a blood sample. Alternative or further patient samples, such as saliva, tissue or other bodily fluids can be collected for analysis by one or more systems of the reader.

The collected blood sample 402 can then be prepared, if necessary or desired, for analysis. The preparation of the blood sample can include increasing the viscosity of the blood 404, which can be done by mixing the collected blood sample with a viscosity reagent, such as glycerol (at any appropriate or desired concentration) or any other fluid, reagent, or chemical that increases the viscosity of the blood sample. In one example, the viscosity reagent does not impact the resulting analysis of the blood sample and assists with preparing the blood sample for analysis. This can include lysing the cells of the blood sample to release the various cellular components for analysis, such as detection or quantification, by the reader. Lysing agents can include fluids, such as water or various chemicals, and powders.

Lysing 406 can be included in the preparation of the blood sample. Lysing can take time, so a requisite amount of time may be required to ensure adequate lysing of parasites, cellular materials, parasitic material, the like, or combinations or multiples thereof has occurred within the blood sample in preparation for analysis. The lysing of the cells of the blood sample can occur naturally, as part of a cellular death or destruction cycle, or can be enhanced or performed using chemical or mechanical lysing techniques. As previously discussed, adequate time can be waited, such as 5 minutes for lysing in water and 15 seconds for mechanical lysing using sonication, to achieve adequate lysing of the cells in the blood sample in preparation for analysis of the sample using the reader. For maximizing hemozoin release in the sample, in addition to the blood cell lysing, the lysing of the malaria parasite and the lysing of the malaria parasite food vacuole is done through the lysing process Light is then transmitted or passed through the blood sample and measured in a varying magnetic field 408, such as by the MOD system 300 of FIGS. 3A-3B. The application of a varying magnetic field to the blood sample can cause magnetic, or paramagnetic, components of the patient, or blood, sample to align with the polarity of the applied magnetic field. The alignment of the magnetic, or paramagnetic, components of the blood sample affects the transmission of light through the blood sample. As such, a differential of light transmittance through the blood sample can be established by transmitting light through the blood sample with the application of a magnetic field in a first state, such as a lower strength or intensity of magnetic field or the absence of a magnetic field, and then applying the same light, same intensity and wavelength, through the blood sample while the magnetic field is applied in a second state, such as a higher strength or intensity of magnetic field or the application of a magnetic field. The differential of the transmitted light through the blood sample in the two states can indicate the presence and amount of a paramagnetic compound(s) within the blood sample. The applied magnetic field can be from one or more permanent magnets or electromagnet(s) that can be energized. Either the blood sample or the magnets can be moveable and in some examples, either is moveable or both are moveable. The magnetic field applied to the blood sample can be attuned to preferentially affect a specific magnetic, or paramagnetic, component(s) of the patient or blood sample. The application or variance of the magnetic field can also affect or impact other portions or components of the patient or blood sample.

The measured light transmission characteristics (raw signal, waveform morphology such as differential amplitudes, amplitude rise and fall times, dwell times at high or low, etc.) can be analyzed to identify signal feature(s) that indicates the presence of a magnetic or paramagnetic component of the analyzed blood sample.

Based on the measured light transmission characteristics, a probability of hemozoin characteristic 412 (e.g., amount of hemozoin, size of hemozoin, source of hemozoin, or the like) can be determined. The probability can be expressed as a numerical value or a subjective likelihood, such as a high or low probability, based on comparing the measured light transmission characteristics to a database of known correlated measured values from different hemozoin characteristics, an algorithm to correlate measured light transmission characteristics with hemozoin characteristics, a statistical analysis of the measured light transmission characteristics to determine the hemozoin characteristic, or repeated analysis of the sample to determine the hemozoin characteristic based on the measured light transmission characteristics which can be further compared to specific and unique templates determined from previously collected hemozoin data. Additional statistical techniques, algorithms or other analysis techniques can be applied using the measured light transmission characteristics, generating new features that can be further used to determine the hemozoin characteristic based on the collected and analyzed blood sample.

Once the analysis of the blood sample is complete, the results can be output 414. The output of the results can include the identified blood characteristic(s) and other information relevant to or determined, calculated, or identified during the analysis of the blood sample (e.g., relaxing time or time period, rise slope, fall slope, time delay, the like, or combinations or multiples thereof). The output can also include a treatment recommendation. The output can be displayed or relayed to the user in a visual output, such as on a display, auditory, such as by a speaker, or other manner. This can include transmitting the output results to an external device, such as a computer, through a wired or wireless connection or communication protocol.

The blood sample can then be further prepared by filtering, such as before the measuring step 408. Filtering the sample can remove one or more components of the sample, such as debris from cell lysing, clots or agglomerations of cells, or other components that could affect the analysis or are otherwise undesirable or unneeded in the sample to be analyzed. An alternative approach is to filter, so the hemozoin for example, are one of the components left. The filter can be an element having structural features, such as pore size, or chemical features that allow the filter to restrain, remove, attract, or otherwise filter a particular component from the patient sample. An example filter can have a pore size of 1-5 microns to filter a patient sample, such as blood. The patient sample or blood can be passed passively, by Brownian motion, or actively, by a pressure differential, through or across a fixed filter to remove the particular component. Alternatively, the filter can move through, about or be placed in the patient or blood sample to filter a component(s) from the sample. Passing through the filter can also cause or enhance cell lysing.

A further preparation of the patient blood sample can include cleaning or concentrating the patient sample prior to analysis. Cleaning or concentrating the patient sample can include removing unwanted components of the patient blood sample prior to analysis. The various unwanted components are typically dispersed throughout the patient's blood and can interfere with an accurate reading of the patient sample. For example, the unwanted components can add noise to the detected data signal, can move in and out of the light transmission path that is transmitted through the sample, or can otherwise obstruct the analysis of the patient sample.

An example cleaning or concentrating the patient sample can include appropriately diluting the patient sample anywhere between 100:1 to 1:1 or any other desired amount. The diluted sample lowers the effective concentration of the compound(s) being studied. The sample is then lysed, such as by sonication. The lysed patient sample is then centrifuged to separate one or more desired components of the patient sample from the remaining portion of the patient sample. The remaining portion of the patient sample, the supernate of the centrifuged sample, can be disposed of so that the one or more desired components of the patient sample remain or the supernate might be the desired component. During centrifuging, hemozoin forms small pellets while some other blood components remain in suspension to form the supernate. The concentrated portion, in this specific example the hemozoin, is then diluted to a desired end volume. The re-diluted hemozoin is sonicated to loosen the hemozoin from the walls of the centrifuge chamber where it tends to adhere during centrifugation. Analysis of the cleaned or concentrated sample can then be performed using one or more systems of the reader.

Another example of cleaning or concentrating the patient sample prior to analysis can include passing the lysed diluted patient sample over a magnetic surface, such as a column of ferrite balls in a magnetic field. The magnetized ferrite surface attracts the magnetic components of the patient sample, while the remainder of the sample passes through which concentrates the magnetic component(s) of the patient sample and separating, or cleaning, the magnetic component(s) from the remainder of the patient sample. The magnetic component(s) of the patient sample can then be washed from the ferrite surface after removing the magnetic field. The sample can then be diluted, which can also be performed by the washing of the magnetic components from the ferrite surface, to an appropriate or necessary volume for analysis. The ferrite surface can also be sonicated or vibrated to assist with removal or washing of the magnetic component of the patient sample from the ferrite surface.

In further embodiments, the measurement chamber can be a chamber within the reader, with the patient blood sample transferred to the measurement chamber of the reader from the cartridge. An interface of the reader or cartridge can transfer a portion of the patient or blood sample from the cartridge into the measurement chamber of the reader. The patient sample can be transferred from the cartridge to the reader using a pressure differential, such as negative pressure in the reader measurement chamber to draw the sample from the cartridge or positive pressure applied to the cartridge to push the patient sample from the cartridge into the reader measurement chamber. The sample can be transferred from the cartridge to the reader through the same opening as the patient sample was originally transferred into the cartridge or through another opening or conduit of the cartridge or the chamber of the cartridge within which the patient sample is contained. Alternatively, the reader can include a piercing element to pierce a portion of the cartridge to withdraw the patient sample, or a portion, from the cartridge.

Figure 5:
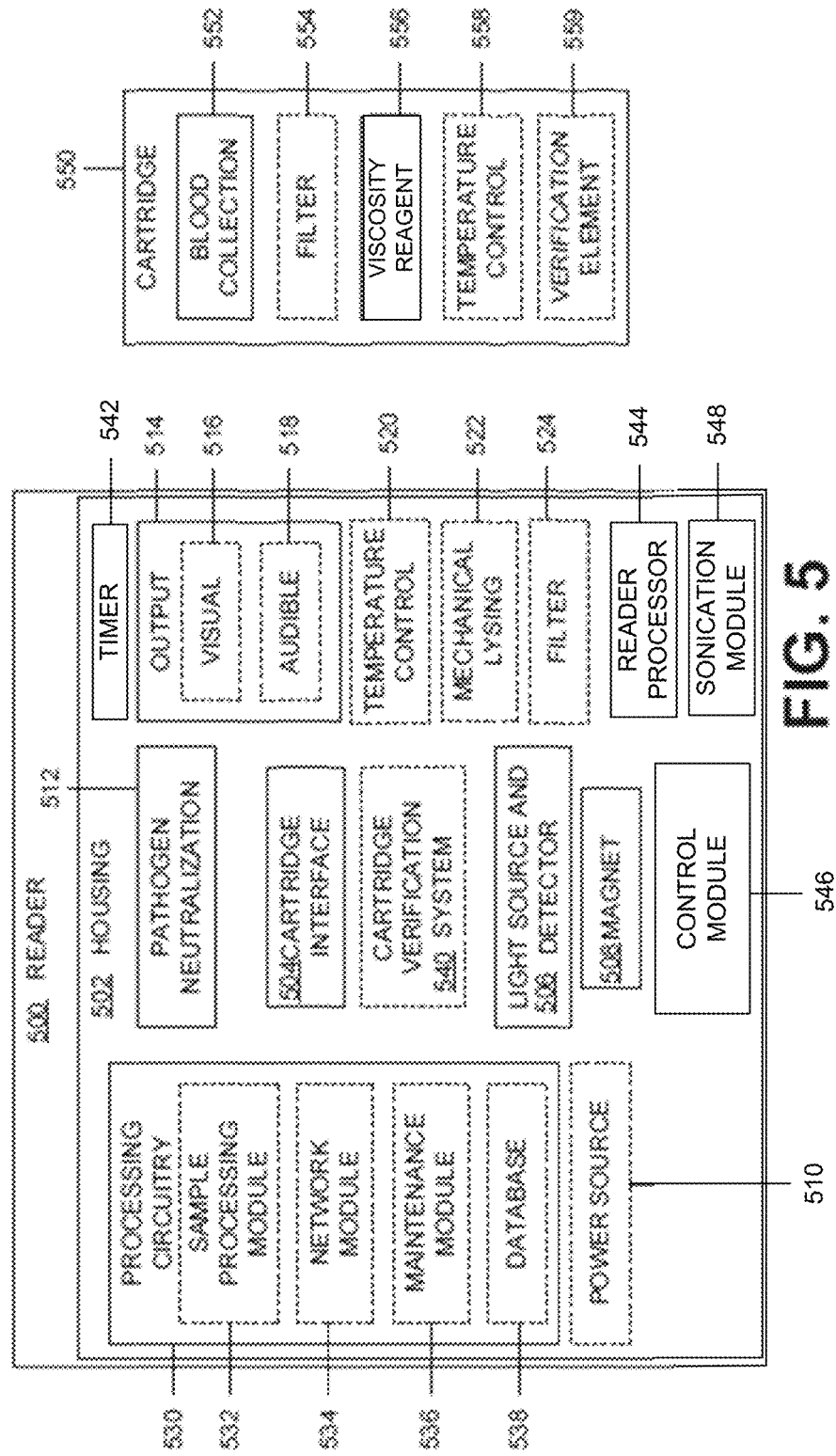
FIG. 5 illustrates a block diagram of an example diagnostics system.

FIG. 5 illustrates an example reader 500 and a cartridge 550. The reader 500 can include all or a portion of the required systems or elements required to perform analysis of a patient sample. The cartridge 550 can include none or a portion of the systems or elements required to perform analysis of the patient sample. The reader 500 and cartridge 550 interface to perform the analysis, such as the method 400 of FIG. 4, of a patient sample.

The reader 500 includes a housing 502 that surrounds and encloses some portion or all of the reader components. FIG. 5 shows that the housing encloses all components of the reader 500, however, one having skill in the art will appreciate that any one or more components can be external to the housing, as needed or desired. As previously discussed, the housing 502 of the reader 500 is constructed of suitable materials in a suitably robust construction such that the reader 500 can be rugged and portable. Example materials that can be included in the housing 502 include plastics, metals, and composites. The housing 502 can be constructed of multiple or a singular material and can include geometry or structural features that enhance the usability of the reader 500. Such features can include a smooth outer surface that is easily cleaned, grips or handles for carrying the reader 500, shock protection or increased structural strength in locations to prevent damage to the internal components of the reader 500, insulation to limit the transfer of heat through the housing 502 or shield magnetic fields sourced within the housing 502, a membrane or construction to prevent the intrusion of moisture and dust into the interior of the reader 502, connections, ports or interfaces for connecting the reader 500 to an external element or device using a physical or wireless connection, instructions regarding the use of the reader 500, identification markings such as a serial number or additional necessary or desirable features that can facilitate the safe, effective, efficient or proper use of the reader 500. The housing 502 can feature access points, such as removable or openable panels, to allow access to the interior of the reader 500 for maintenance or repair of the internal components, elements or systems of the reader 500. Additionally, the housing 502 of the reader 500 can be removable or separable from the other components, elements or systems of the reader 500, allowing the replacement of the housing 502, easing the cleaning of the housing 502, providing access to the components, elements or systems of the reader 500 or other abilities that require or are made easier by the removal of the housing 502 of the reader 500.

The portability of the reader 500 can be an important consideration in the design and packaging of the reader 500, including the housing 502. The reader 500 may need to be rugged and easily transported so that it can be moved to and used in a variety of embodiments. Considerations, such as operating environment and access to infrastructure, can be considered when designing or constructing the reader 500 such that the reader can be used safely, effectively, and efficiently in a variety of environments or locations reliably. Depending on the environment of and infrastructure available in a particular location in which the system is to be used, the housing can be customized to best operate in that location by the addition or modification of existing reader features. Alternatively, the reader 500 can be designed or packaged to be more permanently located, such as in a laboratory, clinic, or other setting.

The housing 502 of the reader 500 includes a cartridge interface 504 that interacts with or engages the cartridge 550 for analysis of a patient sample. The cartridge interface 504 can be a slot that is shaped to receive the cartridge 550. The user inserts the cartridge 550 into the slot in preparation for analysis of the patient sample. The slot can include internal geometry that aligns or orients the inserted cartridge 550 in a proper alignment or orientation for the components, elements or systems of the reader 500 to perform the requisite or desired analysis of the patient sample contained within the cartridge 500. For example, the cartridge interface 504 can accept a variety of cartridges 550 having different cross-sections, such as square, rectangular, and circular cross-sections. The unique shape of each cartridge 550, the unique cross-section, can interact with the geometry of the cartridge interface 504 to properly align the cartridge 550 within the reader 500 for analysis. For example, the circular cross-section cartridge can insert into the cartridge interface 504 to a first position at a first orientation, the square cross-section cartridge can insert into the cartridge interface 504 to a second position at a second orientation. The various orientations and positions that a specific cartridge 550 can be inserted into the cartridge interface 504 can be the same or different for multiple disease-specific cartridges 550.

The reader 500 can also include a cartridge verification system 540. The cartridge verification system 540 can be integrated with or separate from the cartridge interface 504 or included internal to or external from the reader 500. The cartridge verification system 540 can verify the legitimacy of a cartridge to assist with efficient and effective analysis of a patient sample. An example verification system 540 can include a verification element 559 of the cartridge 550 that interacts with the cartridge verification system 540 to verify the cartridge prior to further processing of the patient sample. Once the cartridge is verified, further analysis of a patient sample contained within the cartridge can be allowed to proceed. The verification of the cartridge can be the threshold analysis of the in vitro diagnostics process of the patient sample, in some examples. This verification can include limiting the analysis to a specific single or multiple analyses based on the cartridge verification.

A positive engagement or lock in the reader 500 can engage the cartridge 550 when properly and fully inserted. This engagement can also provide a tactile, audible, or visual cue to the user to signify proper insertion or interfacing of the cartridge 550 and reader 500. An example of a positive engagement or lock can include a notch and protrusion arrangement. The notch can be sized to receive and releasably restrain the protrusion when engaged such that the notch of one element, the reader 500 or cartridge 550, engages the protrusion on the opposite element, reader 500 or cartridge 550, to releasably connect, interface with or engage the two elements, the reader 500 and cartridge 550, together. When prompted, such as when the analysis is completed or an error situation, the user can remove the cartridge 550 from the reader 500.

The cartridge interface 504 can also include an actuator or other element of the reader 500 that assists with the proper insertion or interfacing of the cartridge 550 and reader 500. The actuator can engage the cartridge 550 before the cartridge is fully inserted, the actuator can then position the cartridge 550 in a proper alignment or orientation with the reader 500 for the reader 500 to analyze the patient sample within the cartridge 550. When prompted, such as automatically by the reader 500 or manually by the user, the actuator can "eject" or disengage the cartridge 550 from the reader 500. The disengagement can fully or partially remove the cartridge 550 from the reader 500. Alternatively, the actuator can assist with the engagement or interfacing of the cartridge 550 with the reader 500 and not with the disengagement of the cartridge 550 and reader 500. In this example, the user can be required to remove the cartridge 550 from the reader 500 when prompted.

The cartridge interface 504 can be shaped to engage one or more specific cartridges 550, which prevents the insertion of an incorrect or improper cartridge 550 within the reader 500. The cartridge interface 504 can also be reconfigurable, either manually by a user or automatically by the reader 500 to accommodate a specific cartridge design to perform one or more specific analyses of a patient sample. For example, a user can input a desired or required analysis to be performed on a patient sample, the reader 500 can then reconfigure or prompt the reconfiguration of the cartridge interface 504 to accept a specific cartridge 550 that corresponds to the requested analysis.

For example, the cartridge interface 504 can include multiple configurable elements, such as panels, that can be configured or arranged automatically in response to a received analysis to be performed, such as a user-selected infection or disease for which to analyze the patient sample. The now configured or arranged configurable elements of the cartridge interface 504 are in a specific geometry into which only a compatible cartridge can be inserted. The analysis to be performed can be an input by a user into the reader 500 or from a remote administrator or system. In a further example, a specific cartridge interface 504 can include removable or replaceable cartridge interfaces 504 that can be removed from or inserted in the reader 500. Each cartridge interface can include geometry to accept a specific cartridge design(s). Additionally, the inserted cartridge interface 504 can be detected or otherwise communicated to the reader 500 and the reader 500 can limit available options, such as the analyses that can be performed, based on the inserted cartridge interface 504. Each cartridge interface 504, or cartridge interface 504 design or geometry, can correspond to a specific analysis or analyses. Further, the reader 500 can be limited to the specific analysis or analyses corresponding to the particular cartridge interface 504 or cartridge interface 504 geometry.

In a further example, the cartridge interface 504 can initially accept any inserted cartridge. Once a cartridge is inserted, the cartridge interface 504, a sensor or other reader 500 system or element can detect the cartridge type and the corresponding analysis or analyses that can be performed based on the cartridge type. The cartridge interface 504 can manipulate the cartridge position or orientation, the reader 500 can properly position or orient analysis systems or elements relative to the cartridge, or the cartridge interface 504 or reader 500 systems or elements perform the analysis or analyses corresponding to the cartridge type.

Also, a sample processing module 532 of the processing circuitry 530 of the reader 500, or an external sample processing system or element, can alter the processing of the sample analysis data to correct, compensate or otherwise modify the collected sample analysis data based on the type of cartridge inserted within the reader 500. Instead of or in addition to positioning or aligning the cartridge or reader 500 analysis systems relative to the reader, the processing of the collected sample analysis data can be manipulated or modified to compensate based on the type of cartridge inserted. Additional modifiers can include compensating for position or alignment errors caused by improper positioning or alignment of the cartridge relative to the analysis systems or elements.

The reader 500 can also include a timer 542 to measure one or more time periods during one or more cycles, including, for example, a relaxation time period that begins when the magnetic field is removed or lowered on the blood sample and ends when the light transmission stabilizes at a new value, a stabilization period (i.e., plateau or valley), or the like. The reader 500 can also include a reader processor 544 to output the one or more time periods, these time periods can be variable.

The reader 500 can also include a control module 546. The control module 546 can be a component of a processor, a stand-alone module within the reader 500, or a module that is external to the reader 500, such as on a second device or external memory (e.g., hard drive, sold state drive, flash drive, a server, a cloud storage, or the like).

The control module 546 can process data in real time to determine whether a control parameter can be adjusted or optimized, to determine whether a test can be ended early (i.e., data acquired from the sample is appropriate), to determine whether a test can be extended (e.g., to increase test accuracy), the like, or combinations or multiples thereof. The control module 546 can also determine test run effectiveness (i.e., detect a bad test run, bad cartridge, or both and output an instruction or trigger to perform another test).

To determine whether or not one or more parameters can be adjusted or to determine test run effectiveness, the control module 546 can analyze the real time data, such as by comparing the real time data against a threshold or predetermined value, by extracting and comparing waveform features from the real time data signal, by performing template correlations with the real time data signal (i.e., matching measured data to a template of data to smooth data or remove or reduce noise), look-up tables, the like, or combinations or multiples thereof. Alternatively, or additionally, the sample processing module 532 can analyze the real time data and generate one or more instructions to the control module 546 to adjust or optimize one or more parameters of the reader 500.

The control module 546 can also control, optimize, or control and optimize one or more parameters of the reader 500, a test on the sample, or both. The one or more parameters include magnet motion, magnet speed, number of cycles, data acquisition rates, light source intensity (i.e., brightness), the like, or combinations or multiples thereof. The control module 546 can also perform signal processing, such as baseline wander removal, signal noise reduction techniques and other techniques to make at the first (i.e., earliest) point a call on the absences or detection of the analyte, such as hemozoin.

For example, the control module 546 can adjust motor speed, data acquisition rates, or both in real time, such as during data capture (i.e., during a test of a sample), to improve overall data quality and measurement capability. Additionally, controlling motor speed and position can permit one or more modules of the reader 500 (e.g., sample processing module 532, control module 546, or both) to compare acquired data for increased or enhanced signal-to-noise processing, limit of detection (e.g., threshold or values for analyte detection), the like, or combinations or multiples thereof.

As another example, the control module 546 can control sample illumination, including turning a light source on, turning the light source off, adjusting the light source intensity (i.e., brightness), the like, or combinations or multiples thereof.

The control module 546 can generate instructions, such as to end a test early, extend a test, optimize one or more reader parameters, adjust one or more reader parameters, the like, or combinations or multiples thereof based on the results of the real time data. The instructions can be sent to the component associated with the one or more parameters being optimized to adjust or optimize the one or more parameters. For example, the control module 546 can send an instruction to the magnet 508 to increase speed being moved to and from the sample. As another example, the control module 546 can send an instruction to the light source 506 to increase light intensity, to change the light wavelength (e.g., switch a filter, use a different light source, or the like). As yet another example, the control module 546 can generate an instruction to end a test or continue the test based on the first (i.e., earliest) time point. As another example, the control module 546 can generate an instruction to end a test, continue the test, or extend the test beyond an initial test duration based on the first real time data signal, the second real time data signal, or both.

The reader 500 can also include a sonication module 548. The sonication module 548 controls sonication, detects effectiveness of sonication, retriggers additional sonication cycles before test starts, the like, or combinations or multiples thereof. Alternatively, the sonication module 548 can be external to the reader 500, such as being a component of an external device or system or cloud.

Further, the cartridge interface 504 can include multiple orientation or alignment features that engage specific cartridge 550 features to properly align a specific, inserted cartridge with a specific analysis process. For example, a first cartridge for a first specific analysis is inserted into the cartridge interface 504 which guides, aligns, or orients the first cartridge properly in a first position for the first analysis to be performed, a second cartridge for a second specific analysis can be interested in the same cartridge interface 504, which can properly guide, align, or orient the second cartridge in a second position for the second analysis to be performed. In this manner, the cartridge interface 504 ensures the proper positioning of a variety of specific cartridge designs within the reader 500 allowing a corresponding variety of specific analyses to be performed, each analysis corresponding to one or more specific cartridge designs.

The cartridge interface 504 can also include a number for position points corresponding to various steps of analysis. For example, an analysis can require that the cartridge 550 is inserted partially to a first position within the reader 500 to perform a first step of the analysis, the reader 500 can prompt the user to advance or move the cartridge 550 to a second position, such as further insertion of the cartridge 550 within the reader 500, to perform a further step of the analysis. Each position can include a tactile, audible, or visual indication to a user manually inserting the cartridge 550 within the cartridge interface 504 to assist the user with properly position the cartridge 550 within the cartridge interface 504. An actuator, such as described previously, can position the cartridge 550 at the various analysis require positions automatically, or can assist the user with the cartridge 550 positioning or orientation. The cartridge 550 can be in positioned or oriented in different manners to perform different steps, processes, or actions. For example, the cartridge 550 can be placed in a first position or orientation so the patient sample can be sonicated, then the cartridge 550 can be placed in a second position or orientation so the patient sample can be analyzed.

Insertion of the cartridge 550 into cartridge interface 504 of the reader 500 can automatically initiate or prompt a user to initiate analysis of the patient sample contained within the cartridge 550. An actuator or sensor can be connected to the processing circuitry of the reader 500 and triggered by or sense the insertion of the cartridge 550 to automatically initiate or to prompt a user to initiate the analysis of the patient sample. Initiating analysis of the patient sample can include powering-up, preparing, and running the various analyses systems or devices, such as a light source and detector 506 or mechanical lysing 522. In some examples, the user need only insert the cartridge 550 in the reader 500 to actuate or trigger the entire diagnostics process to an output.

The cartridge interface 504 and additional elements, such as guides or actuators can be integrated into the housing 502 of the reader 500 or can be separate components, elements or systems. Each of the additional elements can be further separable from each other allowing for replacement, substitution, repair or maintenance of the additional elements as necessary or required.

The reader 500 can include a single cartridge interface 504, such as the example shown in FIGS. 1A-1B, or can include multiple cartridge interfaces 504 in the same reader 500. The multiple cartridge interfaces 504 can allow the reader 500 to analyze multiple patient samples simultaneously or in succession by allowing more than one cartridge 550 to be interfaced with the reader 500. Additionally, each of the multiple cartridge interfaces 504 can accept the same or different cartridges to perform the same or different analyses. Further, in conjunction with a multi- or singular cartridge interface 504, a guide, rack, carousel or system can hold multiple cartridges in preparation for analysis. The guide, rack, carousel or system can feed or guide, actively or passively, cartridges 550 to the reader 500 by the cartridge interface 504 allowing multiple patient samples or cartridges 550 to be analyzed with minimal interruption between the analyses.

The reader 500 shown in FIG. 5 includes a light source and detector 506. The light source and detector 506 can be part of a MOD, the optical portion, or other analysis or detection system within the reader 500, to be used in performing analysis of patient samples. The light source, such as a laser, light emitting diode (LED), incandescent bulb, fluorescent bulb, or the like, emits light and the light detector receives light, signals, or outputs from the light detector. The detected light can be used to quantify or characterize the light received by the light detector. In example embodiments, the light source and detector can be arranged opposite one another, separated by a distance along a single axis. In this example, the light detector can receive light emitted from the light source across the distance, which can include an intervening object such as a patient sample. In this example, the LED and detector are positioned on opposing sides across the patient sample contained in the cartridge and the cartridge has an optical window(s) that allow for complete transmission of the laser light through the patient sample. The light transmission path through the patient sample can be entirely through the fluid, below any free surface of the fluid if the sample chamber is not completely full of the patient sample. Alternatively, the light source and light detector can be arranged offset from one another allowing the light detector to quantify or characterize light reflected or refracted by an object, such as a patient sample. Further, multiple light sources or light detectors can be included in the reader 500.

The positioning and structure of the cartridge 550 within the reader 500 can be such that the light source and light detector are positioned relative to the inserted cartridge 550 to ensure that the light transmission path between the light source and light detector passes entirely through the fluid patient sample within the cartridge 550 below any free surface of the patient sample that might exist in the cartridge. The light source can emit a consistent and steady light, which can be further standardized by collimating or polarizing the emitted light that is transmitted through the patient sample and received by the light detector. As light is transmitted through the patient sample, components within the patient sample can absorb, scatter, reflect or otherwise affect the incoming light. The light detector therefore registers an altered quantity or characteristic of the light transmitted through the patient sample than light transmitted directly from the light source to the light detector with no intervening patient sample. The altered quantity or characteristic of light transmitted through the patient sample can be included or used during analysis of the patient sample. Optionally, the emitted light from the light source can be divided, such as by a beam splitter. A first portion of the split beam can be passed through the sample to a first light detector and a second portion of the split beam can be directed to a second light detector with no intervening sample. The transmitted light differential can be measured based on the registered transmittance by the first and second light detectors.

The light source can be one or more light emitting sources, such as an incandescent bulb, a fluorescent bulb, a light emitting diode (LED), a laser, the sun or other light source. In some example embodiments, the light source can emit a steady light having known characteristics or properties. Alternatively, the light source can emit varied light, such as light emitted by an incandescent bulb. The light source can be modulated to change the intensity or wavelength(s) of transmitted light. Such light can be standardized, entirely or in portion, using filters or lenses through which the emitted light is transmitted. For certain analyses, the variance in emitted light properties may not affect the analyses performed, which can be due to the short duration of the analysis or other features of the analysis. An example light source can emit light at a single desired wavelength (e.g., 640 nm). In another example, the light source can emit multiple wavelengths at once, with filters being used to filter out non-desired wavelengths.

The light detector receives light emitted from the light source and then transmitted, refracted or reflected through or from the patient sample. The output from the light detector can be used to quantify or characterize the light received by the detector. Alternatively, the light detector can quantify or characterize the received light itself and output or transmit data or a signal indicative of the quantified or characterized received light. Example light detectors can include photodiodes, digital imaging elements such as a charge coupled device (CCD), a CMOS imager, a photovoltaic array, or other suitable sensors or detectors capable of registering a change in response to received light.

The light source and light detector 506 can be connected to processing circuitry 530 of the reader 500. The processing circuitry 530 can trigger the emission and potentially control the characteristics of light from the light source or receive signals from the light detector based on the quantity or characteristics of light received by the light detector.

Reflective surface(s) can be positioned within the housing 502 or positioned relative to the patient sample such that the light emitted from the light source is transmitted multiple times through the patient sample before being received by the light detector. Each of the multiple transmission paths within the patient sample can occur below a free surface of the sample so the entirety of the multiple light transmission path through the sample occurs within the fluid sample. The geometry of the cartridge can assist to ensure that the laser transmission does not extend above any existing free surface of the patient sample.

The repeated transmission of light through the patient sample assists with the analysis of the patient sample. The repeated transmission of the light through the sample increases the transmission path of the light which can correspondingly increase the sensitivity, reliability or accuracy of the detected light transmission since the light is transmitted through a larger portion or volume of patient sample and has a higher probability of contacting an element or component within the sample that can result in a change in a property or characteristic in the light transmitted through the patient sample.

The reader 500 can include a magnet or magnets 508. The magnet(s) can be included as a portion or part of a MOD, such as the MOD example shown in FIGS. 3A-3B, or used in analysis of a patient sample. The magnet(s) 508 can be movable within the reader 500, allowing the magnet(s) to be moved relative to the patient sample. This can subject the patient sample to the presence of a magnetic field or the presence of a varying magnetic field as the magnet(s) 508 is moved relative to the patient sample. Alternatively, the patient sample can be moved relative to the magnet(s) 508. The magnet 508 can be a permanent magnet and can include a single magnet or multiple magnets. In an example, the magnet includes two permanent magnets, such as the MOD examples taught by U.S. Ser. No. 14/766,523, which is incorporated herein by reference in its entirety. An example MOD includes two permanent magnets that are positioned on opposite sides of a patient sample, which can also be on opposites sides of a cartridge containing a patient sample. The magnet can also be an electromagnet(s) that can be energized as required or desired during analysis of the patient sample. Further, the strength and polarity of the electromagnet can be varied or set to a required or desired level or orientation.

The reader 500 can include an internal power source 510 that supplies the necessary power to run the components, elements or systems of the reader 500 to perform analysis of patient samples or preserve a minimal, required functionality of the reader. The power source 510 can supply power to the processing circuitry 530, the light source and light detector 506, the magnet 508 or other component, elements or systems of the reader 500. The power source 510 can include one or more batteries or other energy storage devices that provide a required or desired level of power for the reader 500. Additionally, the power source 510 or a portion thereof can be external to the reader 500 and connected thereto as needed or required. External power sources can include batteries or other energy storage devices or a connection to a nearby power source such as a generator, municipal power, or solar array.

The reader 500 can also include pathogen neutralization 512. The pathogen neutralization 512 can include physical components, such as a device or system, or a chemical component. There are many different methods of pathogen neutralization and many different devices or systems capable of performing the methods. The goal of pathogen neutralization is to target specific undesirable biological material, such as diseases and parasites, for destruction or neutralization or to destroy biological material indiscriminately, such as by sterilization. Various systems, such as devices or chemicals that interrupt biological processes or cause the breakdown of biological materials can be to neutralize pathogens within a reader 500 or a cartridge 550.

An ultraviolet (UV) light source is an example pathogen neutralization 512 device that could be used within the reader 500. Exposure to UV light has a debilitating effect on biological material and exposure to intense UV light can cause biological destruction. A UV light source can be placed within the reader 500 and activated to bathe the interior of the reader in UV light, which neutralizes at least a portion of the biological material, including pathogens, within the reader 500. Alternatively, the UV light can be continuously powered on when the reader 500 is in use. The UV light can also be targeted, with one or more UV light sources placed in specific areas of the reader 500 to perform the desired pathogen neutralization. Additionally, the UV light can be positioned to penetrate or bathe a cartridge 550 inserted within the reader 500 to neutralize the patient sample within the cartridge 550 after analysis has been performed. A timing device can be connected to the UV light source to ensure that the UV light source is activated for a necessary amount of time to perform the pathogen neutralization. A photo- or light detector can also be included, such as the light detector of the light source and light detector 506, that can monitor the output of the UV light source to check the continued efficacy of the UV light source or monitor the output of the UV light source to ensure it is activated for a long enough duration to achieve a level of pathogen neutralization. The emitted UV light can affect materials, such as plastic, adversely causing them to become brittle. In some examples, shielding can be included within the housing 502 of the reader 500 to protect areas, components, elements or systems which could be damaged by UV light exposure.

A further pathogen neutralization 512 system can include the use of chemicals to neutralize biological material within the reader 500 or cartridge 550. A chemical based pathogen neutralization 512 system can include the application of chemicals within the reader 500 on a temporary or permanent basis. That is, a chemical application can be applied within the reader 500 during manufacture, the applied chemical application can continuously destroy at least a portion of biological material that contacts a surface upon which the chemical was applied. A temporary chemical based pathogen neutralization 512 system can include a chemical dispersal system that deploys or applies chemicals within the reader 500 or cartridge 550 on actuation, the chemicals contact various surfaces, elements, components or systems of the reader 500, destroying at least a portion of biological material thereon.

In an example embodiment, pathogen neutralizing chemicals, such as a bleach-based solution, can be sprayed, fogged, or distributed about the interior of the reader 500 to perform the pathogen neutralization. The pathogen neutralizing chemicals can be added to the reader 500 by a user, contained within a vessel that is housed, inserted within or fluidically connected to the reader 500. The pathogen neutralizing chemicals, such as the bleach-based solution, can be prepared as needed or can be prepared and stored for later use. An indicator or timer can be included that can indicate to a user once the pathogen neutralization process is complete. The indicator or timer can also prevent the use of the reader 500 until the pathogen neutralization process is complete. As with the previously described pathogen neutralization systems, the chemical-based pathogen neutralization method can also neutralize at least a portion of biological material on or within a cartridge 550 inserted within the reader 500. Additionally, the chemical-based pathogen neutralization chemicals can be pumped or transported through the various components, elements or systems of the reader 500, to disinfect portions that can contact a patient sample, which helps to prevent cross-contamination of patient samples.

An example pathogen neutralization system to neutralize at least a portion of the pathogens of the cartridge 550 can include a portion that is included in the cartridge 550. Pathogen neutralization material, such as powders, fluids or other components can be included in the reader 500 or cartridge 550 assist with neutralization of pathogens within the cartridge 550. The pathogen neutralization material can be included in a portion of the cartridge 550 and dispersed into the collected sample or other portions of the cartridge 550 upon actuation, such as by a user, the reader 500, the cartridge 550, or another source. The pathogen neutralization material can also be integrated with a portion of the cartridge, such as included in the viscosity reagent 556. Alternatively, the pathogen neutralization material can be included in the reader 500 and the reader 500 can circulate, or otherwise insert, the pathogen neutralization material into the cartridge 550. The pathogen neutralization material can be targeted to a specific pathogen or be a general wide spectrum pathogen neutralizer.

The reader 500 can include an output 514 that includes one or more visual 516 or audible 518 outputs although in other examples the output is data and does not include visual or audible outputs. The output 514 shown in FIG. 5 communicates information regarding the status of the reader 500, the results of analysis of a patient sample, instructions regarding use of the reader 500 or other information to a user or other computing device. The visual 516 output 514 can include a display, such as a screen, such as a touchscreen, lights, or other visual indicators. The touchscreen used to display information, such as analysis results, to the user can also be used by a user to input to the reader 500. The audible 518 output 514 can include a speaker, buzzer, or other audible indicators. The output 514, visual 516 or audible 518, can be output through an external device, such as a computer, speaker, or mobile device connected physically or wirelessly to the reader 500. The output 514 can output data, including the collected analysis data or interpretative data indicative of the presence or absence of an infection, disease or condition within the patient or the patient sample. An example can include the presence of hemozoin within the patient sample. The interpretive data output can be based on the analysis data collected and processed by the processing circuitry 530 of the reader 500.

The reader 500 can also include temperature control 520. The temperature control 520 can actively or passively control the temperature of at least a portion of the reader 500. Active temperature control 520 can include heating or cooling a portion of the reader 500. Temperature control 520 can also include heating one portion of the reader 500 and cooling another portion of the reader 500. The temperature control 520 can include a refrigeration system, resistive heater, infrared heater, thermoelectric elements, radiator, or other temperature control devices or systems. One example is thermoelectric control of the temperature of the light source which in one example is a laser diode. Passive temperature control can include structures to contain a thermal material in portions of the reader 500. This can include holders for ice, hot water, ice packs, and other thermal materials, the holders retain the thermal material in portions of or about components, elements or systems of the reader 500.

The reader 500 can also include mechanical lysing 522. Mechanical lysing 522 can assist with cell lysing, for example, of cells of a patient blood sample within a cartridge 550 or the lysing of the patient blood sample within the reader 500. Mechanical lysing 522 can include a physical disruptor, or portion thereof, an agitator, a sonicator that can apply sound energy to the patient sample, or other mechanical lysing device or system. The mechanical lysing 522 can interface with or engage the cartridge 550 to facilitate the lysing of the patient sample. The mechanical lysing 522 can be mechanically powered, such as by a wound spring, or electrically powered, such as by a reader 500 power source 510.

The reader 500 can also include a filter 524. The filter 524 can attract, extract, collect or otherwise remove unwanted components or particles in a patient sample of the cartridge 550 or concentrate the wanted components or particles. The filtering of the patient sample by the filter 524 can occur as the patient sample is transferred from the cartridge 550 into the reader 500 or the patient sample can be transferred from the cartridge 550, through the filter 524 and back into the cartridge 550 for analysis. The filter 524 can include structural and chemical features that allow the filter 524 to remove desired or required components from the patient sample. The filter can be affixed in a stationary position to contact the patient sample or moveable through the patient sample to filter the patient sample.

Processing circuitry 530 can be included in the reader 500 to receive input from various components, elements or systems, such as the light source and light detector 506, of the reader 500. The processing circuitry 530 can process the received inputs to perform analysis of the patient sample and output results or data of that analysis. The processing circuitry 530 can include a sample processing module 532, a network module 534, a maintenance module 536 and a database 538. The various elements, 532, 534, 536, 538 and others, of the processing circuitry 530 can be removable or replaceable, allowing replacement and addition of various elements to the processing circuitry 530. In example embodiments, all or a portion of the processing circuitry 530 can be included in the reader 500 and a portion of processing circuitry included in the cartridge 550. The processing circuitry 530 can also control the various components, elements or systems, such as pathogen neutralization 512, mechanical lysing 522, the light source, and others, of the reader 500.

The processing circuitry 530 can initiate or control the analysis of a patient sample within a cartridge 550. The processing circuitry 530 can include preset routines that can be executed by the reader 500 to analyze a patient sample. The preset routines can include prompts for user input or the processing circuitry 530 can prompt a user for input before, during or after analysis of a patient sample. User prompts can include acknowledgement or authorization to proceed through one or more portions of the analysis process. Alternatively, the processing circuitry 530 can initiate, perform, or direct the analysis of the patient sample automatically without user prompts. The processing circuitry 530 can proceed through the various processes and procedures of an analysis of a patient sample, engaging any one or more of the reader 500 systems and collecting the analysis data. The processing circuitry 530 can further automatically process the collected data and transmit a result to a user or other, including an indication the analysis is complete, information regarding the analysis or other indications. The processing circuitry 530 can also transmit the collected data to an external system or device for processing and can transmit a result to the user or the result can be transmitted by one or more of an external system or device.

The sample processing module 532 can receive inputs from the light detector of the light source and light detector 506. Based on the received light detector data, including varying magnetic fields, the sample processing module 532 can determine at least a characteristic of the patient sample, such as a disease or condition, a probability of a characteristic, such as an infection, of the patient sample and quantification of a characteristic, such as a parasite level, of the patient sample. The sample processing module 532 can output an indication of a characteristic, such as an infection, or other various data based on the analysis of the patient sample. The output from the sample processing module 532 can be output through the output 514 of the reader 500 or transmitted to an external device or system, such as a computer, mobile device, and remote server or database.

The sample processing module 532 can analyze the patient sample to determine a hemoglobin characteristic, such as a hemoglobin affecting disease or condition, based on the data from various components, elements or systems of the reader 500. The results of the analysis can be output from the sample processing module 532 to the output 514 to convey the information to a user or other. For example, the sample processing module 532 can use malaria measurement data for anemia detection.

In one example, the sample processing module 532 and the control module 546 can form a feedback loop. As data is processed by the sample processing module 532, the sample processing module 532 can output an instruction to the control module 546 to adjust one or more parameters to obtain a different type of data, better quality data, or both. The control module 546 can also receive data from the sample processing module 532 and adjust one or more parameters based on analysis of the data by the control module 546.

A network module 534 can be included in the processing circuitry 530. The network module can allow the reader 500 to communicate with other readers, computing devices, servers, databases or other devices or systems. The network module 534 can communicate with another device through a physical connection, such as a local area network (LAN), Universal Serial Bus (USB), or wireless, such as Bluetooth®, connection. In an example, the reader 500 can communicate to a remote server through the network module 530 allowing the reader to upload patient sample analysis to the patient's medical records stored on the remote server. The network module 534 can transmit or receive communication to or from the reader 500 and another device or system. In another example, information on the patient can be downloaded to the reader and added to the display or output or used in the analysis(es). For example, demographic information such as age, sex, etc.

A maintenance module 536 can be included in the processing circuitry 530. The maintenance module 536 can perform, initiate or prompt maintenance, calibration, or other processes of the reader 500. Maintenance of the reader 500 can include prompting a user to clean a portion of the reader 500, to replenish resources of the reader 500 and other regular or unscheduled maintenance of the reader 500. Calibration of the reader 500 can include testing components, elements or systems of the reader 500 to check if the reader 500 is in an effective operable state. Additionally, the calibration of the reader 500 can be performed by the maintenance module 536 or prompt a user to perform necessary calibration procedures to allow the reader 500 to perform patient sample analysis effectively and correctly. The maintenance module could also allow automated or semi-automated ordering of supplies or service.

A detection algorithm can be included in the processing circuitry 530, the sample processing module 532, or the control module 546. The detection algorithm can incorporate all features, logic and thresholds or can access a database 538. The database 538 can include a library of hemozoin, data for hemozoin, statistical data, test conditions, and other data. The detection algorithm can determine the amount of hemozoin, size of hemozoin, source of hemozoin, or the like within the blood sample, such as by extracting and comparing waveform features, template correlations (i.e., matching measured data to a template of data to smooth data or remove or reduce noise), look-up tables, and the like. The network module 534 can be used to communicate the measured light transmission signal raw data or the characteristics to a detection algorithm that is remote from the reader, in whole or in part, such as in the cloud for processing.

Statistical data of the database 538 can be by the detection algorithm. This can include tables with reference light transmission amounts or characteristics through various blood samples having determined the hemozoin characteristic.

The scoring system can incorporate one or more measured parameters and weight or rank the parameters to obtain a result. The scoring system can assign a weight or rank to the measured parameters based on the importance of each respective measured parameter in determining the hemozoin characteristic. For example, relaxation time can be the most important measured parameter and is therefore ranked the highest (e.g., ranked 1) or obtains the greatest individual weight (i.e., highest weight of all measured parameters) or a majority weight (e.g., greater than or equal to 50%, where the cumulative weights of the measured parameters equal 100%).

The database 538 can also include specific information, such as prior sample analysis results.

The cartridge 550 can contain the patient sample for analysis. The cartridge 550 can be inserted in the cartridge interface 504 and the patient sample analyzed or transferred to the reader 500 for analysis by the components, elements or systems of the reader 500. The cartridge 550 can include a blood collection device or system 552, a filter 554, a viscosity reagent 556, a temperature control device or system 558 and a verification element 559.

Blood collection 552 of the cartridge 550 can include a device or system for collecting, storing, or analyzing a patient's blood sample, which can include a passive or active blood collection device or system, a blood sample storage chamber, a blood sample analysis chamber or other chambers, devices or systems to assist or facilitate the collection of a blood sample and analysis of the blood sample.

Active blood sample collection can include the use of a needle, capillary tube or pipette. In an example embodiment, the cartridge 550 can include a needle that can be actuated to deploy from the cartridge 550, piercing a patient's skin and extracting a sample that is drawn into the cartridge 550 and stored for analysis. A further active blood sample collection 552 can be a pipette-like system. The user or other can apply pressure to a bulb or deformable portion of the cartridge 550, the release of pressure on the bulb or deformable portion can draw at least a portion of a patient blood sample into the cartridge 550. The patient can be lanced, poked or pierced to cause bleeding, the blood can be sampled to draw at least a portion of the blood into the cartridge 550 for analysis.

The blood collection 552 can include a lancet or a piercing instrument that can pierce skin to cause bleeding. The blood can be collected using the cartridge 550 to obtain the patient blood sample. Collection of the blood sample can include retraction of the lancet or piercing instrument, carrying a portion go the patient blood into the cartridge 550 for analysis. The blood collection 552 can also include a sealed chamber that is sealed and has negative pressure. A needle can pierce the patient and pierce the sealed chamber, the negative pressure of the sealed chamber causing blood to flow into the sealed chamber due to the pressure differential.

The blood collection 552 can also include a capillary tube or plane that can passively collect a blood sample using capillary action. The patient is caused to bleed, such as by a lancet or other inducing technique, and the capillary tube is placed in the blood to draw a sample into the capillary tube of the cartridge 550 for analysis.

The cartridge 550 can include a filter to filter the patient sample within the cartridge 550. The filter can be placed to filter the patient sample as it is drawn into the cartridge 550 through, before or after, for example, the blood collection 552. In another example, the filter 552 can filter the sample after it has been stored in the cartridge 550. As previously described, the filter can include structural or chemical features to filter a patient sample as necessary or desired.

A viscosity agent, such as a reagent 556, to dilute, treat or prepare the patient sample for analysis can be included in the cartridge 550 to be mixed with the collected patient sample. The viscosity reagent 556 can be stored in a viscosity reagent chamber within the cartridge 550 and separate from the patient sample and mixed automatically or manually. The viscosity reagent 556 can be pre-loaded in the same chamber, a mixing chamber or patient sample chamber, that the patient sample will be stored within the cartridge 550. Alternatively, the viscosity reagent 556 can be stored in the cartridge 550 remote from the patient sample storage and mixed with the patient sample. The dispensing of the viscosity reagent 556 into the patient sample can be triggered manually by the user, or automatically, such as by the cartridge 550 or reader 500. Alternatively, or additionally, the viscosity reagent used to prepare the patient sample for analysis can be stored within the reader 500. The reader 500 can add the viscosity reagent to the patient sample within the cartridge 550 or can be added to a sample, or mixing, chamber of the reader 500 into which the patient sample, or portion thereof, from the cartridge 550 is transferred. As with the cartridge 550, the sample, or mixing chamber, of the reader 500 can also be pre-loaded with the viscosity reagent.

The cartridge 550 can also include temperature control 558, which can include active or passive temperature control systems or methods. Passive temperature control 558 can include insulation, structural design features or chemical design features. The passive temperature control 558 can maintain the temperature of the cartridge 550 to preserve a collected patient sample. Active temperature control 558 can include electronic elements, such as thermoelectric elements that can heat or cool at least a portion of the cartridge 550, for example to regulate the temperature of the cartridge 550 or a portion thereof. Temperature control 558 can include heating or cooling the temperature of the cartridge before, during or after the collection of a patient sample or the analysis of the sample. The temperature control 558 interfaces with the reader 500 or an external device to regulate the temperature of the cartridge 550.

Figure 6:
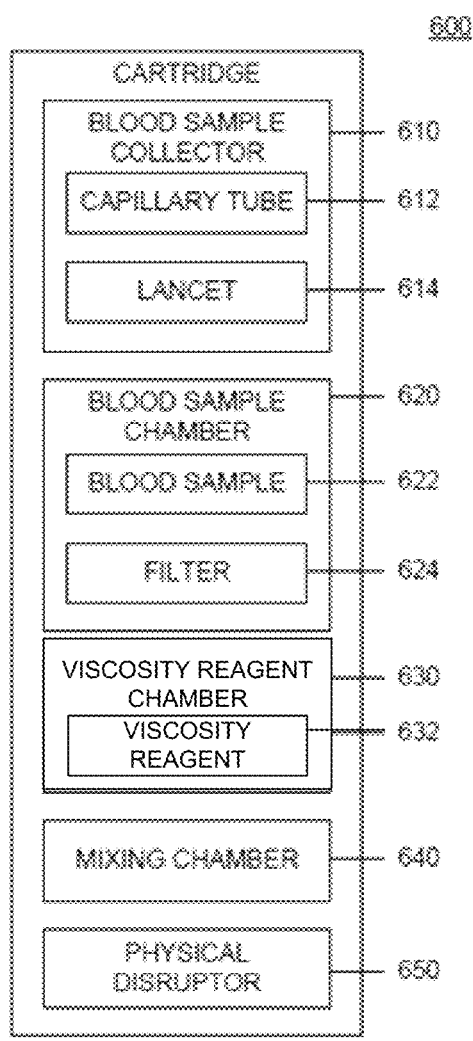
FIG. 6 illustrates a block diagram of another example cartridge.

FIG. 6 is a further example cartridge 600, which can include a blood sample collector 610, a blood sample chamber 620, a viscosity reagent chamber 630, a mixing chamber 640 and a physical disruptor 650. The various components of the cartridge 600 can be arranged in various configurations depending on the analysis to be performed and other environmental or use considerations. In the example shown in FIG. 6, the cartridges 600 components can be interchangeable allowing a complete cartridge 600 to be assembled from various components.

The blood sample collector 610 of the cartridge 600 can collect a blood sample from a patient. The collector 610 can include devices, components or systems to assist or perform the collection of the blood sample from a patient. The blood sample collector 610 can include a capillary tube 612 or a lancet 614. The capillary tube 612 can use capillary action to draw a blood sample into the cartridge 600. The lancet 614 can be used to pierce, puncture or cut a patient's tissue to cause bleeding, from which a blood sample can be taken.

The collected blood sample 622 can be collected in a blood sample chamber 620 of the cartridge 600. The blood sample chamber 620 can include a filter 624 to filter the blood sample 622. The filter 624 can be positioned within the blood sample chamber 620 of the cartridge 600 such that the blood sample chamber 620 is divided into a first and second portion, which are separated by the filter 624. The blood sample chamber 620 can include structural or chemical features to assist with the storage of the blood sample 622 or the analysis of the blood sample 622. Additionally, the blood sample chamber 620 can be located within the cartridge 600 to assist with or facilitate the analysis of the blood sample 622 using a reader.

A viscosity reagent chamber 630 storing viscosity reagent 632 can be included with the cartridge 600. The viscosity reagent 632 within the viscosity reagent chamber 630 can be mixed with the blood sample 622 in the blood sample chamber 620 or the cartridge 600 can include a mixing chamber 640 into which the viscosity reagent 632 and blood sample 622, or portion(s) thereof, can be mixed before, during or after analysis of the blood sample 622. The viscosity reagent 632 can increase the viscosity of the sample.

The cartridge 600 can include a physical disruptor 650 that can assist with the lyses of cells of the blood sample 622 in preparation for analysis. The physical disruptor 650 can include a mechanical, optical, or electrical system or device or portion thereof. In an example, a portion of a physical disrupter system or device can be included with the cartridge 600 and the other portion included on the reader or another external device. An example physical disruptor 650 can include a sonication horn that can direct sonic energy through the blood sample 622 to assist with lysing of the cells of the blood sample 622. The blood sample can undergo physical disruption in other ways as well, including employing maceration techniques and exposing the blood sample to distilled water or chemicals or any combination of desired disruption techniques.

The lysing can occur before or after dilution or other preparation of the blood sample 622. For example, the cartridge might include elements to transmit the maximum ultrasonic energy to the sample trough rods, cones or other shapes in contact with the blood sample.

The various chambers of the cartridge 600 can be interconnected or in fluid communication, allowing or facilitating the movement or transfer of fluid, with one or more of the chambers of the cartridge 600 or a connection to an external fluid source. The fluid communication between chambers can allow the blood sample 622, the viscosity reagent 632 or other fluids to flow or be transferred from chamber to chamber(s) and can include passageways like flexible, rigid, and semi-rigid pipes and tubes. Flow control elements, such as valves, can be positioned along one or more of these passageways to regulate the fluid communication between chambers. The flow control elements can be manually actuated, such as by a reader or user applying pressure to the cartridge 600 or actuating the flow control element, or electrically actuated, such as by a signal from the reader or a user initiated signal or trigger.

FIGS. 7A-7C illustrate testing results for determining one or more hemozoin characteristics. Additionally, the methods and systems can also determine mixed combinations of hemozoin characteristic. For example, the blood sample can include a first set of hemozoin having a first size (e.g., length) and a second set of hemozoin having a second size (e.g., length). The methods and systems can provide results showing the inclusion of both within the blood sample.

Hemozoin contains iron so it can physically respond to the presence of a magnetic field, such as by movement of the magnets, including by the hemozoin being manipulated within a blood sample (or other biological sample). Parasites, such as malaria parasites, transform the heme (iron) waste product from hemoglobin digestion into hemozoin inside food vacuoles. As an example, the hemozoin produced by a first parasite is shorter than the hemozoin produced by a second parasite. Hemozoin from both hemozoin characteristics will rapidly align in the presence of a magnetic field but the size and/or shape may impact alignment. Because of the size and/or shape difference of the hemozoin between the first and second parasites, the hemozoin from first parasite randomizes more quickly than the larger second parasite hemozoin when moved out of a magnetic field. The randomization is due to Brownian motion, which is the random, uncontrolled movement of particles within a fluid resulting from continuous bombardment by other molecules within the same medium. Therefore, with the first parasite the time to change the amount of light passing through the sample from that during a steady state high magnetic field to that during a steady state Low magnetic field, is faster rate than for the larger second parasite.

As a magnetic field is applied to the blood sample, the hemozoin crystals align, causing a change in the transmitted light intensity. When the field is removed, the hemozoin relax back to their random orientations due to the motion (e.g., thermal motion) of the fluid molecules, causing the light intensity to return to its previous value. The time for this relaxation to take place, referred to as the Brownian relaxation time, depends on the size or shape of the hemozoin crystals. The impact of hemozoin crystal length on the Brownian relaxation time of the hemozoin is proportional to the cube of the length of the hemozoin. Since the length of the first parasite crystals are roughly an order of magnitude less than the full length of the second parasite crystals, the Brownian relaxation time of full grown first parasite crystals (i.e., a crystal that formed by the parasite that has fully crystallized) is approximately three orders of magnitude less than the relaxation time of full grown second parasite crystals. In one example, the viscosity of the blood sample can be increased to enhance or increase the Brownian relaxation time between crystal sizes. The viscosity of the blood sample can be increased with glycerol, including varying concentrations thereof, or any appropriate fluid, chemical, or reagent for increasing the viscosity of the blood sample. Though this applies to two infectious species or *Plasmodium* species (e.g., *P. falciparum* and *P. vivax*), this could be further applied to other parasites, sub-species, infectious species, other magnetic or paramagnetic sub-species, the like, or combinations or multiples thereof.

FIG. 7A shows data signals (i.e., normalized intensities, or intensities rescaled to a desired range to aid in comparison of data set), depicted as data plots, for in vitro cultured samples of the second parasite 704 and the first parasite 702 that were lysed and tested in the MOD system 300. The black arrow shown in FIG. 7A indicates when the magnetic field is removed (i.e., turned off), when the sample is moved away from the magnet or magnets, or when the magnetic field is in a "low" state, thus allowing the hemozoin of the second parasite and the first parasite to randomize which permits more light to pass through the sample (i.e., blocks less light; increases light transmission through the samples). The white arrow shown in FIG. 7A indicates when the magnetic field is applied (i.e., turned on), when the sample is moved towards the magnet or magnets, or when the magnetic field is in a "high" state, thus causing the hemozoin of the second parasite and the first parasite to align which inhibits light from passing through the sample (i.e., blocks more light; decrease light transmission through the samples). The data plots depict changes of intensity over time as a magnetic field is applied to and removed from (i.e., magnetic field is removed (i.e., turned off), when the sample is moved away from the magnet or magnets, or when the magnetic field is in a "low" state) a sample including magnetic or paramagnetic components (e.g., hemozoin crystals). When the magnetic field is "on," the hemozoin align and inhibit light transmission through the sample, thereby resulting in a lower intensity. Then, when the magnetic field is "off" or "low" (such as when magnetic field is removed (i.e., turned off), when the sample is moved away from the magnet or magnets, or when the magnetic field is in a "low" state), the hemozoin randomize, due to Brownian motion, and permit light transmission through the sample, thereby resulting in a higher intensity.

The data plots of the first parasite 702 and second parasite 704 are separated because of the difference in Brownian relaxation time or alignment time. Alignment time is the time it takes for hemozoin to go from an unpredictable, unsystematic, or random order or arrangement to a common or similar order or arrangement. For example, when aligned, the hemozoin have a common order or arrangement, including vertical, horizontal, diagonal, or the like. The hemozoin, when aligned, are parallel with each other.

The hemozoin of the first parasite are larger than the hemozoin of the second parasite. Therefore, as the magnetic field is removed (i.e., turned off), the sample is moved away from the magnet or magnets, or when the magnetic field is in a "low" state, the hemozoin of the first parasite either align or randomize slower than the hemozoin.

In one example, the patient sample is subjected to a magnetic field, which is cycled from OFF/ON to ON/OFF to OFF/ON and so on to create multiple data signals. The data signals are then averaged to obtain an ensemble plot for each of the patient samples suspected of including first or second parasites. The ensemble plot can then be used to determine if the patient samples are positive or negative for the first or second parasites.

For a positive determination, the ensemble plot can be used to determine one or more sample metrics. To determine the one or more sample metrics, a feature of the ensemble plot is identified and compared to or normalized to a threshold or other features or characteristics of the known parasite species. The ensemble plot can also undergo signal processing to reduce or eliminate noise, such as by filter, to enhance feature identification, including the type of feature, the location of feature, the amplitude of the feature, or the like.

The sample metrics can use the existing ensemble plot, create new ensemble plots (e.g., adjust raw signal filtering parameters, change baseline wander removal filter parameters, select polarity of ensemble to average, or the like), normalize ensemble plots, calculate an ensemble quality metric based on the ensemble plots (e.g., noise metric, correlation to a quality ensemble, or the like), the like, or combinations or multiples thereof.

A species match metric can then be calculated based on the ensemble correlation or metric to a known parasite species template.

In one example a viscosity of each sample can be increased, such as by the addition of a reagent to increase sample viscosity (e.g., glycerol). The increase in viscosity of the liquid dramatically slows the response time of the much larger hemozoin from the second parasite when the magnetic field is removed (i.e., turned off), when the magnet(s) is moved away from sample, or when the magnetic field is in a "low" state. In the plots, the arrows indicate when the magnet is removed (i.e., turned off), thus allowing the hemozoin of the second parasite and the first parasite to randomize which permits more light to pass through the sample (i.e., blocks less light; increases light transmission through the samples).

The increase in viscosity of the sample can magnify the difference in Brownian relaxation time or alignment time between the larger and smaller hemozoin. Increasing the viscosity increases the forces exerted on the hemozoin. The larger hemozoin are subjected to a larger drag force because of the both the larger size and the increased viscosity. Therefore, the changing of the state of the larger hemozoin (i.e., aligned to randomized, or randomized to aligned) takes more time in order to overcome the larger force exerted on the larger hemozoin. The smaller hemozoin can change state (i.e., aligned to randomized, or randomized to aligned) quicker because of the smaller force exerted on the smaller hemozoin.

The data plots of the first parasite 712 and second parasite 714 are separated because of the difference in Brownian relaxation time. The hemozoin of the first parasite are smaller than the hemozoin of the second parasite. Therefore, as the magnetic field is removed (i.e., turned off), the magnet(s) are moved away from the sample, or when the magnetic field is in a "low" state, the hemozoin of the first parasite either align or randomize quicker than the hemozoin in the second parasite.

The data signals can be processed to remove or reduce noise from the system, which increases or enhances the signal-to-noise ratio (SNR). The noise can be due, at least in part, to optical factors (e.g., spectral, light drift, birefringence), electrical factors (e.g., electrical noise from motors, switching power supplies, wireless components, communication interfaces, induced noise from a changing magnetic field, etc), mechanical factors (e.g., motion caused by a motor, LED or detector circuit board defection due to interactions with the magnetic field), sample factors (e.g., thermal motion of internal sample components, fluid motion), the like, or combinations or multiples thereof. To remove or reduce noise, the data signals can undergo different signal processing techniques that allow improvements in SNR, signal trimming (i.e., removing outlier data based variance from a standard deviation), template correlation (i.e., matching data signal to a template data signal to smooth data or remove or reduce noise), whole ensemble (i.e., average multiple cycles to obtain data, such as corresponding points of different cycles), moving ensemble window (i.e., use set interval of sliding window to obtain data, including average), the like, or combinations or multiples thereof.

The on/off magnetic field cycle or high/low magnetic field cycle can be applied to the patient sample any number of times with the cumulative data undergoing processing, such as processing the complete signal to averaging all of the cycles, to obtain a singular data signal. For example, the on/off magnetic field cycle or high/low magnetic field can be cycled 30 times. The data signals for those 30 cycles are obtained and then averaged at corresponding time points across the 30 cycles to obtain a singular data signal. Each of the cycles can have the same transition for changing the magnetic field or the transition time can be varied from cycle to cycle (e.g., first 15 cycles are 0.4 seconds, cycles 16-30 are 0.2 seconds, and so on) with only cycle times of the same length averaged. Varying transition times can be used to validate or increase the confidence in the determination of the type of hemozoin characteristic by increasing the measured randomization time differences between hemozoin characteristic and other differential light transmission characteristics.

FIG. 7B shows data from a first boxed section 706 of FIG. 7A. As shown, the first and second rising slopes 710, 712 show the change of intensity over time of the first parasite and second parasite data plots 702, 704, respectively, within the first boxed section 706. The first and second parasite species associated with the first and second rising slopes 710, 712 can be determined by one or more techniques, including template matching, thresholding, or the like.

Though the rising or positive slopes depict relaxation time for the respective species, the relaxation time can also be determined by various techniques, such as the area under the curve (e.g., a smaller slope in absolute value provides for a greater area under the curve, where a larger slope in absolute value provides for a lesser area under the curve). Additionally, slope segments, rather than the entirety of a slope can be used to differentiate between hemozoin characteristics. One skilled in the art can use numerous approaches to determine this or an equivalent measure.

FIG. 7C shows data from a first boxed section 7086 of FIG. 7A. As shown, the first and second falling slopes 720, 722 show the change of intensity over time of the first parasite and second parasite data plots 702, 704, respectively, within the first boxed section 708. The first and second parasite species associated with the first and second falling slopes 720, 722 can be determined by one or more techniques, including template matching, thresholding, or the like.

Though the falling or negative slopes depict alignment time for the respective species, the alignment time can also be determined by various techniques, such as the area under the curve (e.g., a smaller slope in absolute value provides for a greater area under the curve, where a larger slope in absolute value provides for a lesser area under the curve). Additionally, slope segments, rather than the entirety of a slope can be used to differentiate between hemozoin characteristics. One skilled in the art can use numerous approaches to determine this or an equivalent measure.

A metric of the ensemble plots can be calculated and used to correlate to a known parasite species. The metric can be based on the derivative of the ensemble rising edge (measure slope of ensemble rising edge for a fixed or variable window), a time constant or relaxation time on the falling edge, based on the derivative of the ensemble falling edge (measure slope of ensemble falling for a fixed or variable window), based on the ensemble width at one to a plurality of points, based on the ensemble amplitude, the like, or combinations or multiples thereof. The metric can be compared against the metric of a known parasite species to determine the unknown parasite species.

The rising slopes, falling slopes, or both can be used to determine the species associated with the hemozoin within the patient sample.

Furthermore, though relaxation or alignment times are discussed, other factors can be used in addition to or alternatively to relaxation or alignment times. Other factors include template matching, machine learning (including decision trees, neural networks, or the like) falling slope (i.e., slope of falling or decreasing transmission intensity), time delay between applying magnetic field and change in light transmission, time delay between removing magnetic field and change in light transmission, the like, or combinations or multiples thereof.

Template matching is when an experimental data signal is matched to one or more templates data signals to determine the type of hemozoin characteristic associated with the experimental data signal. Template matching can be based on percentage of equivalence between the experimental data signal and a template data signal, selecting a template data signal having a higher probability with the experimental data signal, or both. For example, it can be determined that the blood sample includes a first parasite by matching an experimental data signal obtained from a blood sample to a template data signal of the first parasite based on the highest number of equivalences. The experimental data signal can be compared against multiple template data signals, such as by the highest number of overlapping data points, best data plot fit, or the like. It can then be concluded that the parasite associated with the hemozoin of the experimental data signal is the same as the parasite associated with the hemozoin of the template data signal because of the highest number of equivalencies.

Time delay between removing or reducing the magnetic field (i.e., magnet is removed or "off", sample is moved away from the magnet(s), or the magnetic field switched to "low") and change in light transmission is the time gap from the removal of the magnetic field to when the light transmission begins to increase due to the beginning of the randomization of the hemozoin due to Brownian motion. The light transmission does not immediately increase when removing or reducing the magnetic field. In other words, the hemozoin do not go from aligned to randomized instantaneously. The time from which the magnetic field is removed or reduced (i.e., the point at which the hemozoin are aligned) to the time light transmission intensity increases (i.e., the point at which the hemozoin are randomized due to Brownian motion) can be different for different parasites. Therefore, the parasite can be identified by determining the time delay and comparing it against a known threshold or known value or range of values for the parasite . . . .

Time delay between applying a magnetic field (i.e., magnet is applied or "on"; or, magnetic field switched to "high") and change in light transmission is the time gap from the application or introduction of the magnetic field to when the light transmission begins to decrease due to the beginning of the alignment of the hemozoin, which blocks light transmission through the blood sample. For example, a time delay is measured to be 0.1 seconds. The first parasite has, for example, a time delay less than or equal 0.15 seconds, and the second parasite has, for example, a time delay greater than 0.15. Therefore, it can be determined that the blood sample includes the first parasite based on the experimental time delay. Determination of the time delay between applying the magnetic field and change in light transmission can be enhanced by driving or moving a permanent magnet or pair of permanent magnets more quickly into place or by using an electromagnet to turn the magnetic field on instantaneously. For example, applying the magnetic field more gradually permits the hemozoin characteristic to align at a substantial comparable rate regardless of hemozoin size. However, applying the magnetic field more instantaneously permits the hemozoin characteristic to align at a rate inversely proportional to the size (i.e., smaller hemozoin can align quicker than larger hemozoin) due, at least in part, to the smaller change in inertia required for alignment, to the smaller friction force on the smaller hemozoin crystals, or the like.

Signal amplitude can also be used to differentiate between hemozoin characteristics. The signal amplitude can determine an absolute or relative amount of hemozoin, such as by comparing experimental signal amplitude data against known signal amplitude data. For example, a first intensity is known to be associated with 10 micrograms of hemozoin crystal per milliliter. During experimentation, a sample allows for the transmission of light having the first intensity. Therefore, it can be determined that the sample has 10 micrograms of hemozoin crystal per milliliter. As another example, a first sample allows for the transmission of light having a first intensity and a second sample allows for the transmission of light having a second intensity. When the first intensity is greater than the second intensity, it can be determined that the first sample has less hemozoin than the second sample (i.e., fewer hemozoin allow for greater light transmission). The amplitude can also be used a secondary differentiator to change or determine an amplitude threshold, to aid in determining probability between hemozoin characteristics.

Time to signal stabilization can also be used to differentiate between hemozoin characteristics. The plateaus (upper, substantially flat portions) and valleys (lower, substantially flat portions) can be longer or shorter for different aspects of a hemozoin characteristic (e.g., longer vs. shorter, more vs. less, etc.). For example, a first parasite species has a longer plateau than a second parasite species. An experimental data signal having a longer plateau can indicate that the sample includes the first parasite species.

A value or indication of the hemozoin characteristic (e.g., size, amount, associated parasite, etc.) can also be output to a user. The output can include information relevant to or determined, calculated, or identified during the analysis of the blood sample (e.g., relaxing time or time period, rise slope, fall slope, time delay, the like, or combinations or multiples thereof). After experimentation and analysis, a processor can generate and transmit a signal, including the hemozoin characteristic information, to an output for relay to the user in a visual, auditory, or tactile manner. This can include transmitting the output results to an external device, such as a computer, through a wired or wireless connection or communication protocol.

Determining the type of hemozoin characteristic can also help to dictate an appropriate treatment. For example, a first parasite species can be treated with a first type of medication without risk of relapse. However, a second parasite species requires a second type of medication, since treatment of the second parasite species with only the first type of medication can result in a relapse of the infection. The second type of medication, while effective against the second parasite species, has negative effects or contraindications against approximately 20% of those who take it. Therefore, it may be advantageous to perform additional patient testing to ensure that the patient does not have any underlying conditions or physiology which can result in detrimental effects to the patient.

Though certain elements, aspects, components or the like are described in relation to one embodiment or example, such as an example system, those elements, aspects, components or the like can be including with any other systems, such as when it desirous or advantageous to do so.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents.

What is claimed is:

1. A diagnostic system, comprising:
a processor configured to:
    determine a feature of a first slope of a data signal, the first slope representative of a response to a change in a magnetic field applied to a patient sample, the data signal representative of measurements of a feature of a hemozoin produced by the malaria species over a time measurement, the time measurement taken from a time the magnetic field applied to the patient sample is removed or lowered to a time a relaxation light transmittance value reaches a relaxation threshold or an alignment threshold,
    determine a relaxation time or an alignment time of the hemozoin based on the time measurement, and
    determine a malaria species based on the first slope; and an output configured to output the malaria species.

2. The system of claim 1, wherein the feature of the hemozoin produced by the malaria species over the time measurement is associated with an amount of the hemozoin produced by the malaria species, a size of the hemozoin produced by the malaria species, a shape of the hemozoin produced by the malaria species, or combinations or multiples thereof.

3. The system of claim 1, wherein the processor is further configured to reduce signal noise of the data signal.

4. The system of claim 3, wherein the signal noise is reduced by baseline wander removal by applying a signal filter.

5. The system of claim 1, wherein the processor is further configured to generate an instruction to end a test, continue the test, or extend the test beyond an initial test duration based on the data signal, the test generating the data signal representative of the measurements of the feature of the hemozoin produced by the malaria species over the time measurement.

6. The system of claim 1, wherein the processor is further configured to:
identify an undesired fluctuation or shape in the data signal, and
generate a notification to re-test the patient sample based on the undesired fluctuation or shape in the data signal.

7. The system of claim 6, wherein the undesired fluctuation or shape in the data signal is caused by voltage saturation, voltage drift, a bad cartridge, a new sample is required, or combinations or multiples thereof.

8. The system of claim 1, wherein the relaxation threshold represents a starting light transmittance value or range of values that is measured before the magnetic field is applied to the patient sample.

9. The system of claim 1, wherein the relaxation threshold represents a Brownian relaxation threshold or range of values that indicates that the hemozoin within the patient sample has a random or aligned orientation in response to the magnetic field.

10. The system of claim 1, wherein the processor is further configured to determine the relaxation time or the alignment time of the hemozoin, the relaxation time based on a comparison of the determined relaxation time or alignment time to a known value or range of values of a known infection characteristic-specific relaxation or alignment time.

11. The system of claim 1, wherein the output is further configured to output the malaria species correlated with the relaxation time or the alignment time.

12. The system of claim 1, wherein the processor is further configured to generate a diagnostic recommendation based on the malaria species.

13. The system of claim 12, wherein the output is further configured to output the diagnostic recommendation.

14. The system of claim 1, wherein the processor is further configured to generate an instruction to cause a viscosity agent to be dispensed into the patient sample, the dispensed viscosity agent causing a viscosity of the patient sample to increase when mixed with the viscosity agent.

15. The system of claim 1, wherein the output includes an external device having a display.

16. The system of claim 1, wherein the processor is further configured to:
determine the feature of the first slope for a plurality of data signals, the plurality of data signals generated in response to respective cycles between a first amplitude and a second amplitude of the magnetic field, each of the cycles having a respective time measurement over which the respective relaxation light transmittance values reach the relaxation threshold or the alignment threshold,
determine the relaxation time or the alignment time for the hemozoin for each of the respective time measurements, and
determine the malaria species based on the first slope for multiple of the plurality of data signals.

17. The system of claim 16, wherein the processor is further configured to generate an ensemble signal that includes the plurality of data signals.

18. The system of claim 17, wherein the processor is further configured to reduce ensemble noise of the ensemble signal.

19. The system of claim 16, wherein the first amplitude of the magnetic field is greater than the second amplitude of the magnetic field, and wherein the first slope is a positive or rising slope.

20. The system of claim 16, wherein the first amplitude of the magnetic field is less than the second amplitude of the magnetic field, and wherein the first slope is a negative or falling slope.

21. The system of claim 1, wherein the processor is further configured to:
determine a feature of a second slope of the data signal, the second slope representative of a response to another change in the magnetic field applied to the patient sample, and
determine the malaria species based on the first slope and the second slope.

22. The system of claim 1, wherein the processor is further configured to:
determine a characteristic of the data signal that indicates presence of a hemozoin correlating to the malaria species in the patient sample, and
determine the malaria species based on the first slope of the data signal and the characteristic of the data signal that indicates the presence of the hemozoin associated with the malaria species in the patient sample.

23. A method for analyzing a patient sample, the method comprising:
determining a feature of a first slope of a data signal, the first slope representative of a response to a change in light transmitted through a patient sample, the change due to a change in a magnetic field applied to the patient sample, the data signal representative of measurements of a feature of a hemozoin produced by the malaria species over a time measurement, the time measurement taken from a time the magnetic field applied to the patient sample is removed or lowered to a time a relaxation light transmittance value reaches a relaxation threshold or an alignment threshold;
determining a relaxation time or an alignment time of the hemozoin based on the time measurement;
determining a malaria species based on the first slope; and
outputting the malaria species.

24. The method of claim 23, further comprising outputting a diagnosis, a treatment, or both based on the hemozoin of the malaria species, the malaria species, or both.

25. The method of claim 23, further comprising determining the data signal includes a characteristic that indicates presence of the hemozoin of the malaria species in the patient sample.

* * * * *